(12) United States Patent
Nishioka et al.

(10) Patent No.: US 9,200,077 B2
(45) Date of Patent: *Dec. 1, 2015

(54) INJECTABLE SOLUTION CONTAINING THERAPEUTIC AGENT FOR OSTEOARTHRITIS

(75) Inventors: Kusuki Nishioka, Tokyo (JP); Kazuo Yudo, Yokohama (JP)

(73) Assignee: AXIS, Inc., Kagoshima (JP)

( * ) Notice: Subject to any disclaimer, the term of this patent is extended or adjusted under 35 U.S.C. 154(b) by 47 days.

This patent is subject to a terminal disclaimer.

(21) Appl. No.: 13/575,620

(22) PCT Filed: Jan. 27, 2011

(86) PCT No.: PCT/JP2011/000453
§ 371 (c)(1),
(2), (4) Date: Sep. 27, 2012

(87) PCT Pub. No.: WO2011/093081
PCT Pub. Date: Aug. 4, 2011

(65) Prior Publication Data
US 2013/0011416 A1  Jan. 10, 2013

(30) Foreign Application Priority Data
Jan. 29, 2010 (JP) .................................. 2010-018600

(51) Int. Cl.
*C07K 16/28* (2006.01)
*A61K 9/00* (2006.01)
*C07K 16/40* (2006.01)
*A61K 39/00* (2006.01)

(52) U.S. Cl.
CPC ........... *C07K 16/2878* (2013.01); *A61K 9/0019* (2013.01); *C07K 16/40* (2013.01); *A61K 2039/505* (2013.01); *C07K 2317/75* (2013.01); *C07K 2317/76* (2013.01)

(58) Field of Classification Search
None
See application file for complete search history.

(56) References Cited

U.S. PATENT DOCUMENTS

| 5,476,865 | A | 12/1995 | Panetta et al. | |
|---|---|---|---|---|
| 6,086,877 | A * | 7/2000 | Nishioka et al. | 424/156.1 |
| 7,445,794 | B1 * | 11/2008 | Newell et al. | 424/450 |
| 2007/0286867 | A1 | 12/2007 | Johnston et al. | |
| 2008/0292730 | A1 * | 11/2008 | Bentley | 424/684 |

FOREIGN PATENT DOCUMENTS

| CN | 1167115 A | 12/1997 |
|---|---|---|
| CN | 1203922 A | 1/1999 |
| EP | 0799891 A1 | 10/1997 |
| JP | 4-502408 A | 5/1992 |
| JP | 07-194384 A | 8/1995 |
| JP | 8-40897 A | 2/1996 |
| JP | 10-146194 A | 6/1998 |
| JP | 10-155492 A | 6/1998 |
| JP | 11-004694 A | 1/1999 |
| JP | 2004-59582 A | 2/2004 |
| JP | 2004-227311 A | 10/2004 |
| JP | 2005-034154 A | 2/2005 |
| JP | 2006-151843 A | 6/2006 |
| JP | 2007-000141 A | 1/2007 |
| JP | 2007-51077 A | 3/2007 |
| JP | 2007-512303 A | 5/2007 |
| JP | 2007-204398 A | 8/2007 |
| JP | 2007-537134 A | 12/2007 |
| JP | 2008-516593 A | 5/2008 |
| JP | 4560822 B2 | 8/2010 |
| WO | 90/07861 A1 | 7/1990 |
| WO | 03/103710 A | 12/2003 |
| WO | 03/103710 A1 | 12/2003 |
| WO | 2004/017996 A1 | 3/2004 |
| WO | 2005-011721 A2 | 2/2005 |
| WO | 2006/040357 A2 | 4/2006 |
| WO | 2010/013498 A1 | 2/2010 |

OTHER PUBLICATIONS

Umlauf et al. Cartilage biology, pathology, and repair. Cell Mol Life Sci. Dec. 2010;67(24):4197-211. Epub Aug. 25, 2010.*
U.S. Appl. No. 13/575,620, filed Sep. 27, 2012.*
Nakajima, Toshihiro, et al.; "Apoptosis and Functional Fas Antigen in Rheumatoid Arthritis Synoviocytes"; Arthritis & Rheumatism, vol. 38, No. 4, Apr. 1995; XP055033017; pp. 485-491 (6 pages).
Hashimoto, Hideo, et al.; "Soluble Fas Ligand in the Joints of Patients With Rheumatoid Arthritis and Osteoarthritis"; Arthritis & Rheumatism, vol. 41, No. 4, Apr. 1, 1998; XP055033066, ISSN: 0004-3591, DOI: 10.1002/1529-0131(199804)41:4<657::AID-ART 12>3.0.00;2-N; pp. 657-662 (6 pages).
Pennock, Andrew T., et al.; "Role of Apoptotic and Matrix-Degrading Genes in Articular Cartilage and Meniscus of Mature and Aged Rabbits During Development of Osteoarthritis"; Arthritis & Rheumatism, vol. 56, No. 5, May 1, 2007; XP055033483, ISSN: 0004-3591, DOI: 10.1002/art.22523; pp. 1529-1536 (8 pages).
Conway, James G., et al.; "Inhibition of Cartilage and Bone Destruction in Adjuvant Arthritis in the Rat by a Matrix Metallaproteinase Inhibitor"; The Journal of Experimental Medicine, Rockefeller University Press, vol. 182, Aug. 1, 1995; XP000574663, ISSN: 0022-1007, DOI: 10.1084/JEM.182.2.449; pp. 449-457 (9 pages).
Kuo, Po-Lin, et al.; "Fraxetin inhibits the induction of anti-Fas IgM, tumor necrosis factor-a and interleukin-1 b-mediated apoptosis by Fas pathway inhibition in human osteoblastic cell line MG-63"; International Immunopharmacology, Elsevier, vol. 6, No. 7, Jul. 1, 2006; XP024976874, ISSN: 1567-5769; DOI: 10.1016/J.INTIMP. 2006.02.010; pp. 1167-1175 (9 pages).

(Continued)

*Primary Examiner* — David Romeo
(74) *Attorney, Agent, or Firm* — Osha Liang LLP

(57) ABSTRACT

Injections for treating and preventing diseases classified as any of grade 1 to 3 according to the ICRS classification of osteoarthritis, diseases classified as any of grade 1 to 3 according to the Kellgren-Lawrence classification of osteoarthritis or diseases classified as any of grade 1 to 3 according to the Outerbridge classification of osteoarthritis contain anti-Fas IgM antibody as an active ingredient and a pharmaceutically acceptable carrier to alleviate osteoarthritis symptoms by inhibiting the production of cartilage matrix degrading enzymes and by increasing the production of cartilage matrix.

6 Claims, 7 Drawing Sheets

(56) References Cited

OTHER PUBLICATIONS

Fujisawa, Koushi, et al.; "Therapeutic Effect of the Anti-Fas Antibody on Arthritis in HTLV-1 tax Transgenic Mice"; Journal of Clinical Investigation, American Society for Clinical Investigation, vol. 98, No. 2, Jul. 15, 1996; XP000676461, ISSN: 0021-9738, DOI: 10.1172/JCI118789; pp. 271-278 (8 pages).
Supplementary European Search Report dated Jun. 11, 2013, by the European Patent Office, Munich, in related European Patent Application No. EP-11736796 (4 pages).
International Search Report w/translation from PCT/JP2011/000453 dated Mar. 15, 2011 (4 pages).
A. Fukuda, et al.; "Henkeisei Kansetsusho Kenkyu no Genjo OA to Hakotsu Saibo—OA Chiryoyaku no Aratana Target" (translated as Osteoarthritis and osteoclast); Shukan Igaku no Ayumi, vol. 211, No. 4, pp. 285-288; 2004 (4 pages).
Patent Abstracts of Japan Publication No. 2007-204398 dated Aug. 16, 2007 (1 page).
Patent Abstracts of Japan Publication No. 2004-277311 dated Oct. 7, 2004 (2 pages).
Patent Abstracts of Japan Publication No. 2006-151843 dated Jun. 15, 2006 (1 page).
Patent Abstracts of Japan Publication No. 2007-051077 dated Mar. 1, 2007 (1 page).
T. Nakajima, et al.; "Apoptosis and Functional Fas Antigen in Rheumatoid Arthritis Synoviocytes"; Arthritis & Rheumatism, vol. 38, No. 4, pp. 485-491; Apr. 1995 (7 pages).
G. Lisignoli, et al.; "Anti-Fas-Induced Apoptosis in Chondrocytes Reduced by Hyaluronan"; Arthritis & Rheumatism, vol. 44, No. 8, Aug. 2001, pp. 1800-1807 (8 pages).
Patent Abstract of Japan English Abstract for JP2004-059582, published Feb. 26, 2004 (1 page).
Espacenet English Abstract for CN1167115, published Dec. 10, 1997 (1 page).
Espacenet English Abstract for CN1203922, published Jan. 6, 1999 (1 page).
Patent Abstracts of Japan English Abstract for JP 07-194384, published Jan. 8, 1995 (1 pages).
Patent Abstracts of Japan English Abstract for JP 11-004694, published Jan. 12, 1999 (1 page).
Patent Abstracts of Japan English Abstract for JP 2005-034154, published Feb. 10, 2005 (1 page).
Patent Abstracts of Japan English Abstract for JP 2007-000141, published Jan. 11, 2007 (1 page).
Patent Abstracts of Japan English Abstract for JP 10-155492, published Jun. 16, 1998 (1 page).
Patent Abstracts of Japan English Abstract for JP 10-146194, published Feb. 6, 1998 (1 page).
First Official Action issued Jul. 16, 2013, by the State Intellectual Property Office of the People's Republic of China in related Chinese Patent Application No. 201180007596.2, with a partial English translation (9 pages).

* cited by examiner

Fig. 1
Fig. 1A 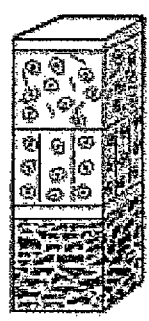 Fig. 1B 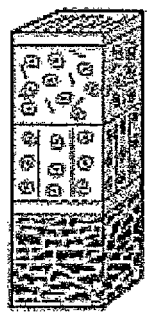 Fig. 1C 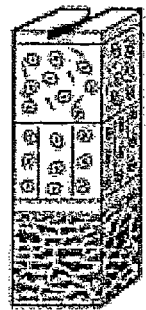 Fig. 1D 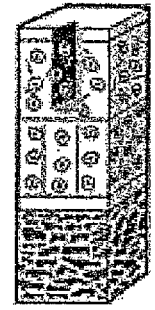
Fig. 1E 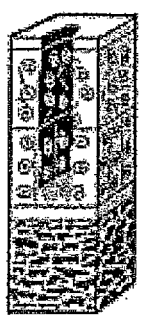 Fig. 1F  Fig. 1G 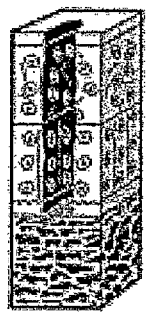 Fig. 1H 
Fig. 1I  Fig. 1J 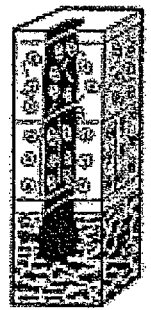

Fig. 2
Fig. 2A
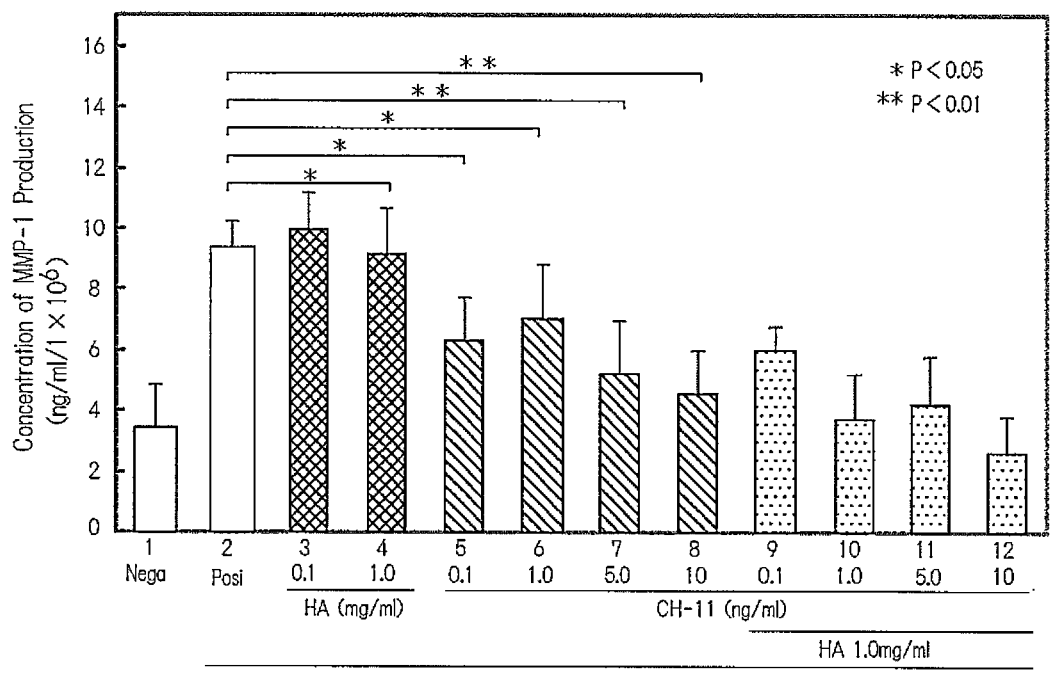
Fig. 2B
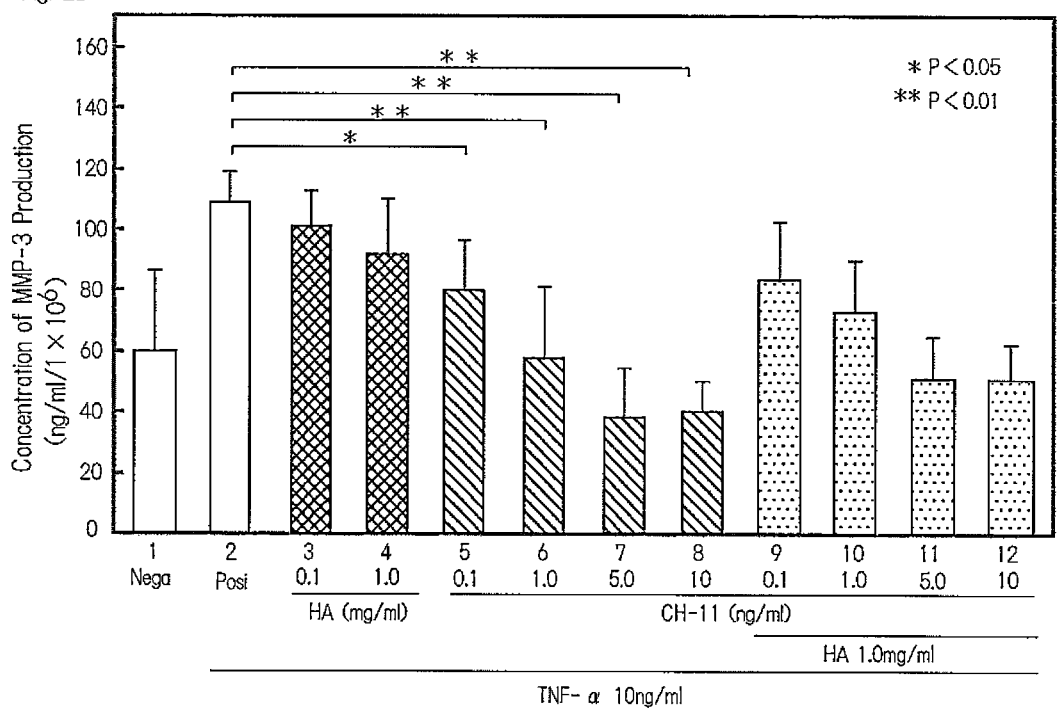

Fig. 5
Fig. 5A
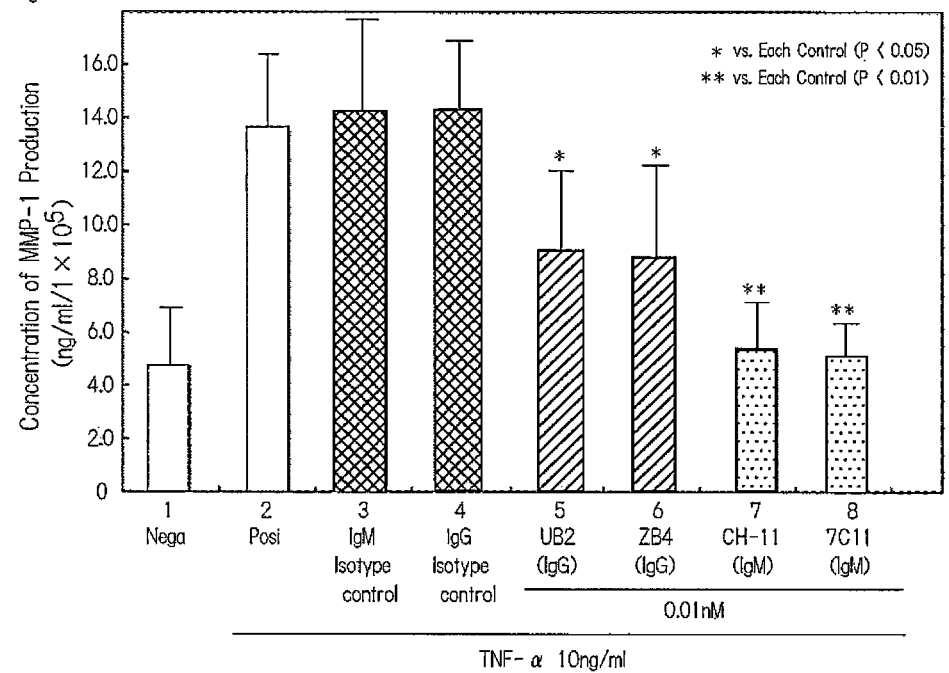
Fig. 5B
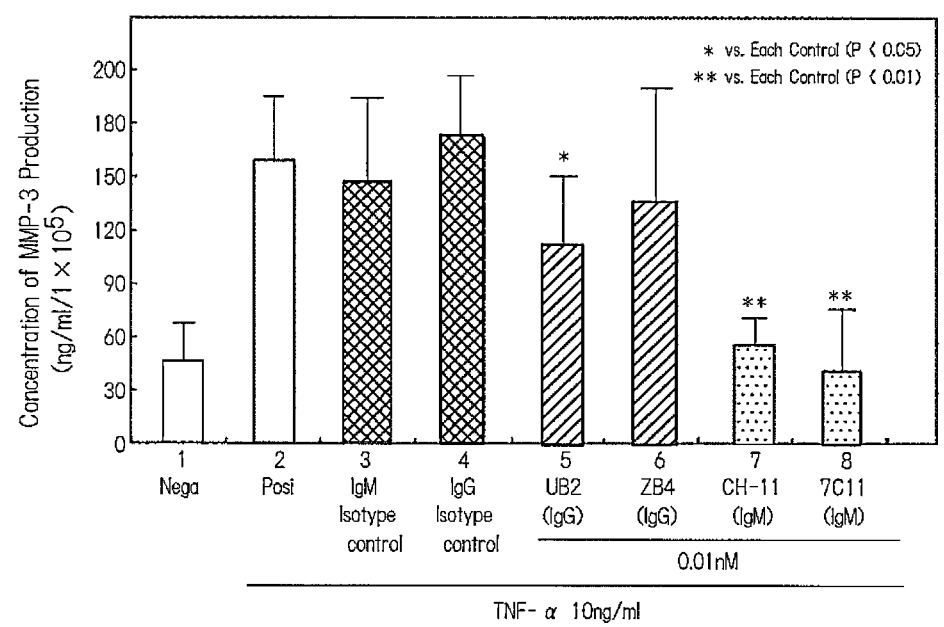

Fig. 6
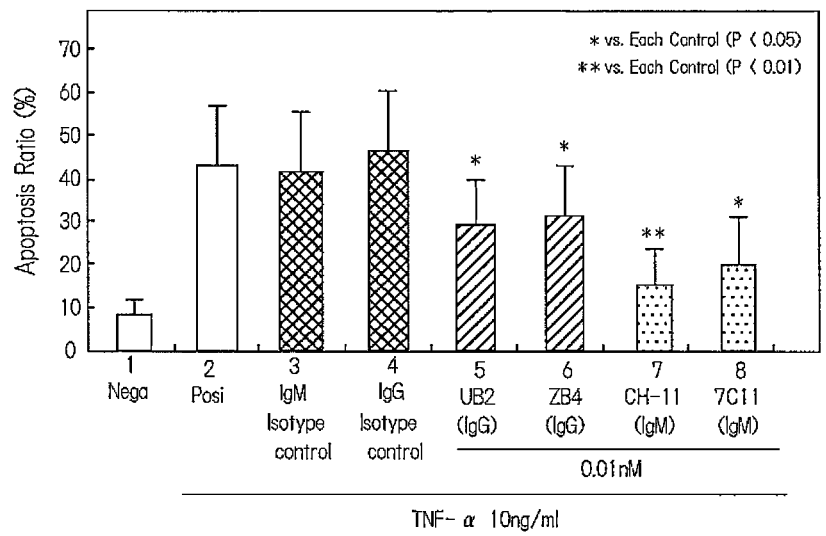
Fig. 7
Fig. 7A
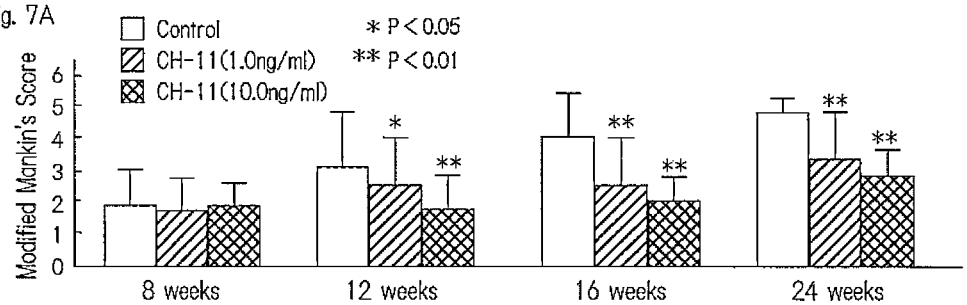
Fig. 7B
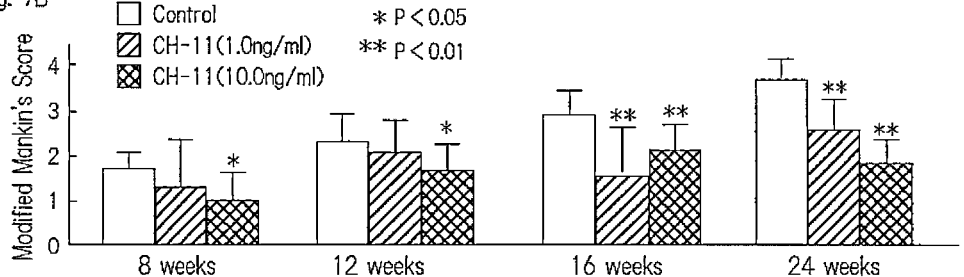
Fig. 7C
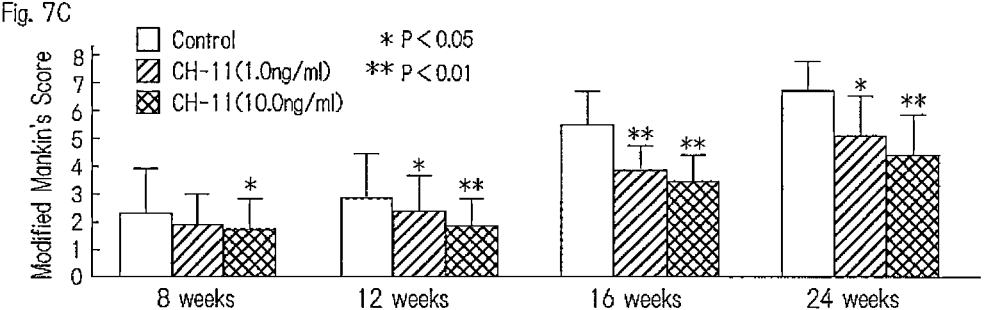

Fig. 8
Fig. 8A  Fig. 8B  Clustering of cartilage cells
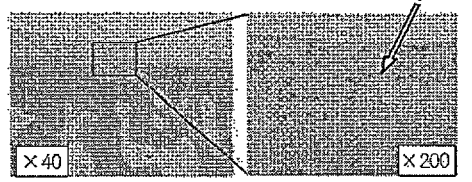
Fig. 8G  Fig. 8H
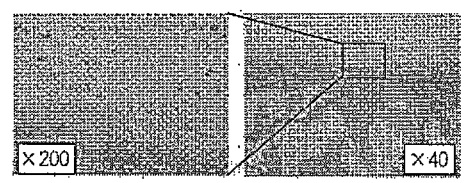
Fig. 8C  Fig. 8D
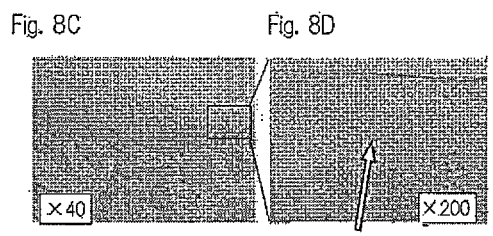
Disappearance of cartilage cells
Fig. 8I  Fig. 8J
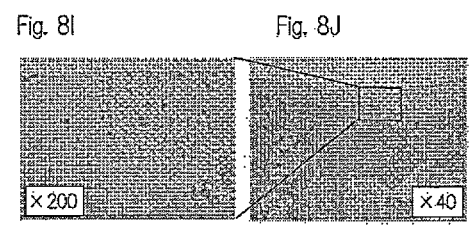
Fig. 8E  Fig. 8F  Disappearance of cartilage cells
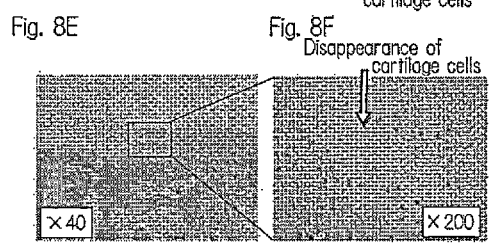
Fig. 8K  Fig. 8L
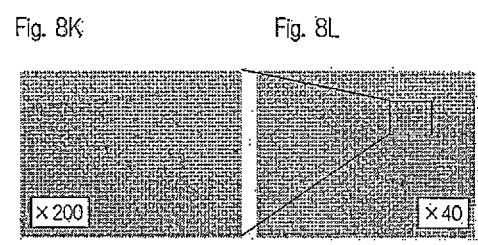
Fig. 8M  Fig. 8N
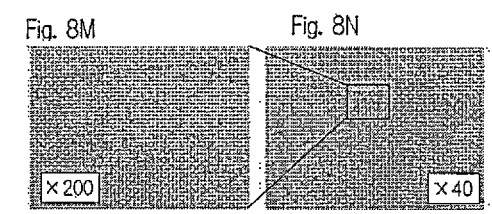
Fig. 8O  Fig. 8P
Disappearance of cartilage cells
Decrease SO stainability
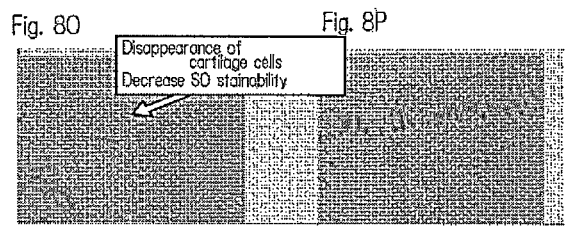

Fig. 9
Fig. 9A  Fig. 9B
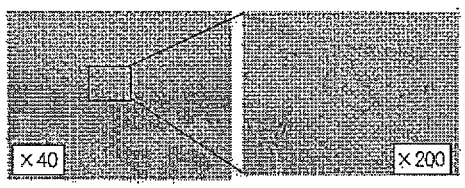
Fig. 9I  Fig. 9J
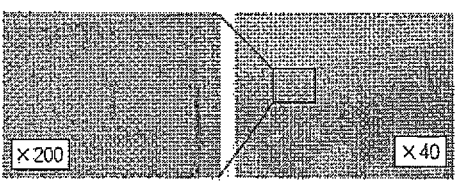
Fig. 9C  Fig. 9D
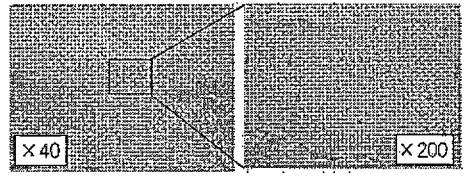
Fig. 9K  Fig. 9L
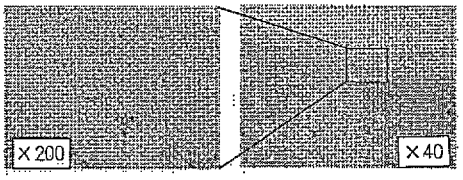
Fig. 9E  Fig. 9F
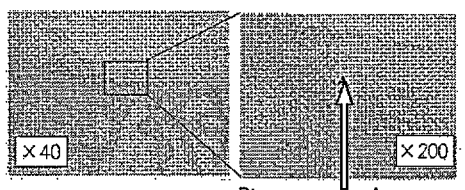
Disappearance of cartilage cells
Fig. 9M  Fig. 9N
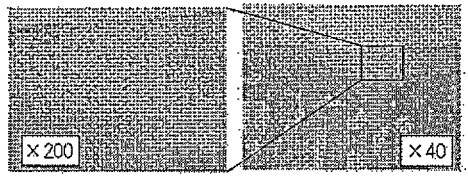
Fig. 9G  Fig. 9H
Disappearance of cartilage cells
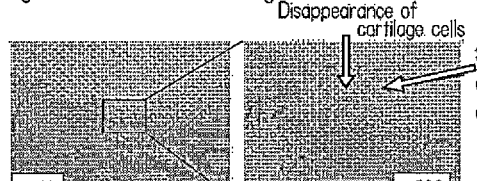
Structure degeneration of cartilage matrix
Fig. 9O  Fig. 9P
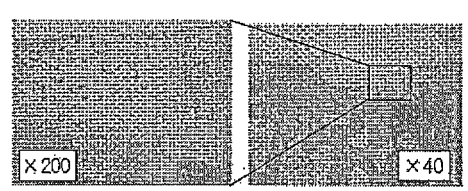

INJECTABLE SOLUTION CONTAINING THERAPEUTIC AGENT FOR OSTEOARTHRITIS

CROSS REFERENCE TO RELATED APPLICATIONS

This is a national stage application based on PCT/JP2011/000453, filed on Jan. 27, 2011, which claims priority to Japanese Patent Application No. 2010-018600,filed on Jan. 29, 2010. This application claims the priority of these prior applications and incorporated their disclosures by reference in their entireties.

TECHNICAL FIELD

The present invention relates to an injection containing treatment agent for osteoarthritis and arthritis (arthromeningitis) derived from osteoarthritis containing an anti-Fas IgM antibody as an active ingredient.

BACKGROUND ART

Osteoarthritis (OA) is a disease caused by aging or mechanical stress resulting in collapse of the articular cartilage surface and proliferation of the new peripheral cartilage associated therewith, articular deformity and breakdown in articular conformity, further progressing to arthrosynovitis. On the other hand, rheumatoid arthritis (RA), typical arthropathy, resulting from immune abnormality or infection, causes inflammatory cell infiltration in synovium, enhances synovial fibroblast proliferation associated with the vascularization, promotes bone or cartilage destruction, and brings an irreversible damage to the joint. Thus, rheumatoid arthritis is an autoimmune disease called inflammatory disease while osteoarthritis is called non-inflammatory disease. Accordingly, treatment agents used in the treatment of rheumatoid arthritis is generally considered to have no treatment effect on osteoarthritis.

Various pharmaceutical composites have been conventionally developed for the purpose of the treatment of rheumatoid arthritis (RA). One example of such pharmaceutical compositions is an anti-Fas antibody (Kokai (unexamined patent publication) No. 2004-59582 (see Patent Document 1)). However, an anti-Fas antibody is reported to have an apoptosis-inducing effect on the synovial cells extracted from the patient with rheumatoid arthritis, but have no apoptosis-inducing effect on the synovial cells extracted from the patient with osteoarthritis (NAKAJIMA et al., "APOPTOSIS AND FUNCTIONAL FAS ANTIGEN IN RHEUMATOID ARTHRITIS SYNOVICYTES", ARTHRITIS & RHEUMATISM, 38 (4), 1995, p. 485-p. 491 (refer to Non-Patent Document 1)).

On the other hand, non-steroidal anti-inflammatory drugs (NSAIDs) having anti-inflammatory and analgesic effects have been used in the treatment of osteoarthritis. In addition, treatments such as removing joint fluid by injection etc. or injecting adrenal corticosteroid or articular cartilage protective agents such as chondoitin sodium sulfate or hyaluronic acid (HA) have been carried out.

Furthermore, a p21-activated kinase (PAK) inhibitor (Kohyo (national publication of translated version) No. 2007-537134 (refer to Patent Document 2)) which is a signaling inhibitor, or a pharmaceutical composition containing anti-sense polynucleotide, ribozyme, low molecule interference RNA, etc. (Kohyo (national publication of translated version) No. 2008-516593 (refer to Patent Documents 3)) have been used as treatment agents against osteoarthritis. However, sufficient effect has not been obtained so far.

In addition, in the development of treatment agents currently in progress, there has been development of treatment agents targeting promoting factors of cartilage reproduction such as interleukin (IL)-1 or attempts to apply the factors inducing cartilage repair or reproduction to drugs. However, satisfactory results have not been obtained so far.

PRIOR ART

Patent Documents

Patent Document 1: Kokai (unexamined patent publication) No. 2004-59582
Patent Document 2: Kohyo (national publication of translated version) No. 2007-537134
Patent Document 3: Kohyo (national publication of translated version) No. 2008-516593
Patent Document 4: Kokai (unexamined patent publication) No. H8-40897
Patent Document 5: Kokai (unexamined patent publication) No. 2006-151843
Patent Document 6: Kokai (unexamined patent publication) No. 2007-51077

Non-Patent Documents

Non-Patent Document 1: NAKAJIMA et al., "APOPTOSIS AND FUNCTIONAL FAS ANTIGEN IN RHEUMATOID ARTHRITIS SYNOVICYTES", ARTHRITIS & RHEUMATISM, 38(4), 1995, p. 485-p. 491
Non-Patent Document 2: ARTHRITIS RHEUM, 2001, VOL. 44, No. 8, pp. 1800-1807

DISCLOSURE OF THE INVENTION

Problems to be Solved by the Invention

It is an object of the present invention to provide an effective injection which is effective in a treatment or prevention of osteoarthritis and arthritis (arthromeningitis) derived from osteoarthritis. Furthermore, it is another object of the present invention to provide an injection containing an inhibitory agent against cartilage matrix degeneration, a cartilage matrix synthesis improving agent, an inhibitory agent against cartilage degeneration and an apoptosis inducing agent against macrophage induced by osteoarthritis.

Means for Solving Problems

The present invention is based on a knowledge that the use of an anti-Fas IgM antibody can control cartilage degeneration in osteoarthritis. Specifically, the present invention is based on a knowledge that the use of an anti-Fas IgM antibody can control cartilage matrix degrading enzyme production. Moreover, the present invention is based on a knowledge that the use of an anti-Fas IgM antibody can improve the ability to produce an cartilage matrix. Moreover, the present invention is based on a knowledge that the apoptosis of the macrophage induced by osteoarthritis can be promoted. The knowledge that an anti-Fas IgM antibody can be used in osteoarthritis is one acquired first this time.

The first aspect of the present invention relates to an injection. The injection comprises a treatment agent or preventive agent for treating or preventing the disease classified into the early stage to the advanced stage of osteoarthritis, containing an anti-Fas IgM antibody as an active ingredient. Each stage from the initial stage to the advanced stage of osteoarthritis is classified according to the ICRS classification, the Kellgren-Lawrence classification, the Outerbridge classification, or the modified Mankin score of osteoarthritis. When the initial stage to the advanced stage of osteoarthritis is classified according to the above classification, the diseases which the agent of the present invention are: (1) diseases classified into grades 1-3 in the ICRS classification of osteoarthritis; (2) diseases classified into grades 1-3 in the Kellgren-Lawrence classification of osteoarthritis; (3) diseases classified into grades 1-3 in the Outerbridge classification of osteoarthritis; or (4) diseases classified into grades 1-7 in the modified Mankin score of osteoarthritis.

In osteoarthritis, the diseases classified into any of the above-mentioned grades or scores are accompanied with cartilage degeneration as condition of disease. The IgM antibody of the present invention can control cartilage degeneration as mentioned below. Therefore, the agent of the present invention containing an anti-Fas IgM antibody as an active ingredient can be used effective to treat or prevent the diseases accompanied with cartilage degeneration. That is, the agent of the present invention can be used effectively to treat or prevent the diseases classified into the initial stage to the advanced stage of osteoarthritis.

Moreover, an anti-Fas IgM antibody can control the production of matrix metalloproteinase (MMP)-1 and MMP-3 which are mediators of cartilage degeneration, as shown in the examples below. MMP is one kind of cartilage matrix degrading enzymes. As the cartilage matrix degradaing enzyme decomposes an articular cartilage, it may be the cause of inducing osteoarthritis or worsening condition of osteoarthritis. Therefore, as an anti-Fas IgM antibody can control the production of MMP, it can be preferably used as a treatment agent or prevention agent for the diseases accompanied by osteoarthritis. Moreover, as shown in the examples below, an anti-Fas IgM antibody can improve the ability to synthesize cartilage matrix proteoglycan. In osteoarthritis, the destruction of articular cartilage may also be the cause. The improvement of the ability to synthesize cartilage matrixes reproduces the destroyed articular cartilage. Therefore, the agent of the present invention can be used effectively to treat or prevent the diseases classified into the initial stage to the advanced stage of osteoarthritis. That is, the present invention also provides the cartilage destruction inhibitory agent containing an anti-Fas IgM antibody as an active ingredient.

The preferred mode of the first aspect of the present invention is the agent as mentioned above, wherein an anti-Fas antibody is an antibody against a peptide consisting of an amino acid sequence which is the same as an extracellular domain (an amino acid sequence depicted in amino acids 26-173 of SEQ ID NO: 1), or an amino acid sequence where its one amino acid residue is replaced, deleted, added, or inserted.

The preferred mode of the first aspect of the present invention is the agent as mentioned above, wherein the anti-Fas IgM antibody is CH11 or 7C11. As shown in the examples below, CH11 or C711 can effectively control the production of MMP1 and MMP3. And CH11 can improve the ability to synthesize a cartilage matrix proteoglycan. Therefore, the agent of the present invention can be used effectively to treat or prevent the diseases classified into the initial stage to the advanced stage of osteoarthritis accompanied with cartilage degeneration.

The second aspect of the present invention is an inhibitory agent against production of a cartilage matrix degrading enzyme production containing an anti-Fas IgM antibody as an active ingredient. As shown in the example below, the anti-Fas IgM is preferably CH11 or 7C11. As demonstrated by the examples, the anti-Fas IgM antibody of the present invention can effectively control the production of cartilage matrix degrading enzyme. Therefore, the agent of the present invention can suitably be used as an inhibitory agent against cartilage matrix degrading enzyme production.

The third aspect of the present invention is a cartilage matrix production agent and an inhibitory agent against cartilage degeneration derived from osteoarthritis containing an anti-Fas IgM antibody as an active ingredient. As shown in the example below, the anti-Fas IgM is preferably CH11. As demonstrated by the examples, the anti-Fas IgM antibody of the present invention can improve the ability to reproduce a cartilage matrix (proteoglycan). Therefore, the agent of the present invention can suitably be used as a cartilage matrix production agent.

The fourth aspect of the present invention is an apoptosis induction agent against the macrophage induced by osteoarthritis containing an anti-Fas IgM antibody as an active ingredient. As shown in the example below, the anti-Fas IgM is preferably CH11 or 7C11. As demonstrated by the examples, the anti-Fas IgM antibody of the present invention can induce the apoptosis of a macrophage induced by osteoarthritis. Therefore, the agent of the present invention can suitably be used as an apoptosis induction agent against the macrophage induced by osteoarthritis.

Effect of the Invention

The present invention can provide an injection that has a treatment agent or a preventive agent for osteoarthritis. Furthermore, the present invention can provide an inhibitory agent against cartilage matrix degeneration, a cartilage matrix synthesis improving agent, and an apoptosis inducing agent against macrophage induced by osteoarthritis.

BRIEF DESCRIPTION OF THE DRAWINGS

FIGS. 1A-1J are figures showing pathological conditions of articular cartilage for every ICRS grade. FIG. 1A shows the cartilage in normal state with grade 0. FIG. 1B shows the cartilage in the state where there are gentle hollows in the surface with grade 1. FIG. 1C shows the cartilage in state where there are cracks in the surface of cartilage with grade 1. FIG. 1D shows the cartilage in the state where the cartilage defect has reached a depth of up to 50% of cartilage with grade 2. FIG. 1E shows the cartilage in the state where the cartilage defect has reached a depth of 50% or more of cartilage with grade 3. FIG. 1F shows the cartilage in the state where the cartilage defect has reached the calcified layer with grade 3. FIG. 1H shows the cartilage in the state where the swelling has been caused with grade 3. Fig. 1I and Fig. 1J show the cartilage in the state where the pathological lesion reached the subchondral bone with grade 4.

FIG. 2 are graphs replaced with drawings showing how an anti-Fas IgM antibody influences the ability to produce matrix metalloproteinase (MMP) of cartilage cells. FIG. 2A is a graph replaced with a drawing showing how an anti-Fas IgM antibody influences the ability to produce MMP1. FIG. 2B is a graph replaced with a drawing showing how an anti-Fas IgM antibody influences the ability to produce MMP3.

FIG. 5 are graphs replaced with drawings showing how an anti-Fas IgM antibody or an anti-Fas IgG antibody influences the ability to produce matrix metalloproteinase (MMP) of cartilage cells. FIG. 5A is a graph replaced with a graph showing how an anti-Fas IgM antibody or an anti-Fas IgG antibody influences the ability to produce MMP1 of cartilage cells. FIG. 5B is a graph replaced with a graph showing how an anti-Fas IgM antibody or an anti-Fas IgG antibody influences the ability to produce MMP3 of cartilage cells.

FIG. 6 is a graph replaced with a drawing showing the apoptosis suppression effect of an anti-Fas IgM antibody or an anti-Fas IgG antibody.

FIG. 7 are graphs replaced with drawings showing the pathological tissue score of an osteoarthritis model rat. FIG. 7A shows the result of Safranine O staining. FIG. 7B shows the result of cartilage cell defect. FIG. 7C shows the result of cartilage structure.

FIG. 8 are photographs replaced with drawings showing the histopathological specimens of osteoarthritis model rats in 12 weeks after treatment. FIGS. 8A-8F show the histopathological specimens of osteoarthritis model rats of control. FIGS. 8G-8J show the histopathological specimens of osteoarthritis rats of a CH-11 low-dose administration group (CH-11: dose of 1.0 ng/ml). FIGS. 8K-8N show the histopathological specimens of osteoarthritis rats of show the histopathological specimens of osteoarthritis model rats of a CH-11 high-dose administration group (CH-11: dose of 10.0 ng/ml). FIG. 8O shows the histopathological specimen of an osteoarthritis model rat of control. FIG. 8P shows the histopathological specimen of an osteoarthritis model rat of a CH-11 low-dose administration group (CH-11: dose of 1.0 ng/ml).

FIG. 9 are photographs replaced with drawings showing the histopathological specimens of osteoarthritis model rats in 24 weeks after treatment. FIGS. 9A-9H show the histopathological specimens of osteoarthritis model rats of control. FIGS. 9I-9L show the histopathological specimens of osteoarthritis rats of a CH-11 low-dose administration group (CH-11: dose of 1.0 ng/ml). FIGS. 9M-9P show the histopathological specimens of osteoarthritis rats of show the histopathological specimens of osteoarthritis model rats of a CH-11 high-dose administration group (CH-11: dose of 10.0 ng/ml). FIG. 9B, FIG. 9D, FIG. 9F, FIG. 9H, FIG. 9I, FIG. 9K, FIG. 9M, and FIG. 9O are enlarged photographs replaced with drawings of portions surrounded by a square of FIG. 9A, FIG. 9C, FIG. 9E, FIG. 9G, FIG. 9J, FIG. 9L, FIG. 9N, and FIG. 9P, respectively.

BEST MODE FOR CARRYING OUT THE INVENTION

Figure 3:
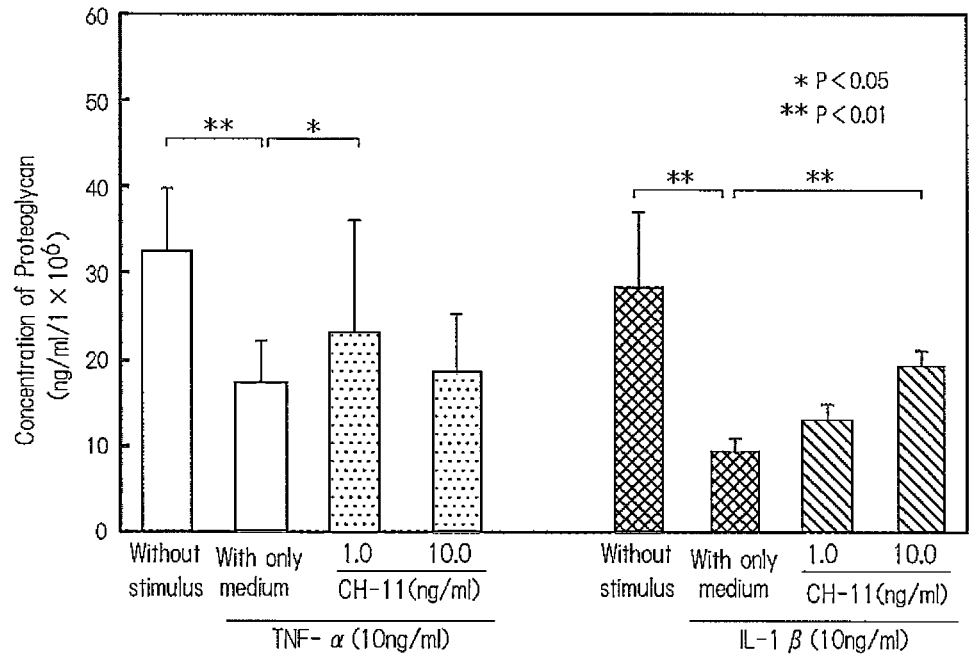
FIG. 3 is a graph replaced with a drawing showing the effect of an anti-Fas IgM antibody on the reduced ability to produce cartilage matrix (proteoglycan).

Hereinafter, the present invention will be explained. The first aspect of the present invention relates to an injection for treating or preventing the disease classified into the early stage to the advanced stage of osteoarthritis, containing an anti-Fas IgM antibody as an active ingredient. Osteoarthritis is a disease developing in the interphalangeal joint, the first carpometacarpal joint, the intervertebral disk of the spine or the lumbar spine, the first metatarsophalangeal joint, the hip joint, and the knee joint. The agent of the present invention can be used in these sites. Among these, the agent of the present invention is preferably used in the hip joint, knee joint or the knee cartilage.

The diseases the agent of the present invention targets are those classified into the early stage to the advanced stage of osteoarthritis accompanied with cartilage degeneration. The stages of osteoarthritis are classified as shown in the following Tables 1-4 based on the pathological condition. Hereinafter, the stages of osteoarthritis will be explained using the staging standards shown in the following Tables 1-4.

Table 1 shows the grading (hereinafter also referred to as "ICRS classification") of cartilage defects in osteoarthritis by ICRS (International Cartilage Repair Society).

TABLE 1

| ICRS classification | |
|---|---|
| Grade 0 | Normal |
| Grade 1 | Nearly normal |
| | Pathological changes in the surface |
| | Gentle hollows |
| | Cracks in the surface |
| Grade 2 | Abnormal |
| | Pathological changes expanded to a depth of up to 50% of cartilage |
| Grade 3 | Severely abnormal |
| | Cartilage defect expanded to a depth of 50% or more of cartilage |
| | Further expanded to the calcified layer |
| | But not expanded to subchondral bone |
| | Including swelling as well |
| Grade 4 | Severely abnormal |
| | Pathological changes expanded to subchondral bone |

According to the ICRS classification, osteoarthritis is classified into grades 0-4. In the ICRS classification, grade 0 is the stage where osteoarthritis has yet to develop. Grade 1 is the early stage of osteoarthritis. Grades 2-3 are the advanced stages of osteoarthritis. Grade 4 is the late stage of osteoarthritis. As mentioned above, the targets of the agent of the present invention are the diseases classified into the early stage to the advanced stage of osteoarthritis. That is, the targets of the agent of the present invention are the diseases classified into any one of grades 1-3 under the ICRS classification of osteoarthritis.

The conditions of the cartilage indicated by each grade of the ICRS classification of osteoarthritis are shown in FIG. 1. The cartilage has a layer structure consisting of a surface layer, an inner layer, a deep layer, and a calcified layer (FIG. 1A). And the cartilage is connected with the bone (subchondral bone) through the calcified layer. FIG. 1A shows the cartilage in normal state with grade 0. FIG. 1B shows the cartilage in the state where there are gentle hollows in the surface with grade 1. FIG. 1C shows the cartilage in state where there are cracks in the surface of cartilage with grade 1. FIG. 1D shows the cartilage in the state where the cartilage defect has reached a depth of up to 50% of cartilage with grade 2. FIG. 1E shows the cartilage in the state where the cartilage defect has reached a depth of 50% or more of cartilage with grade 3. FIG. 1F shows the cartilage in the state where the cartilage defect has reached the calcified layer with grade 3. FIG. 1H shows the cartilage in the state where the swelling has been caused with grade 3. Fig. 1I and Fig. 1J show the cartilage in the state where the pathological lesion reached the subchondral bone with grade 4. As mentioned above, the agent of the present invention treats and prevents cartilage degeneration. As demonstrated in the examples below, the agent of the present invention controls the pathological conditions of osteoarthritis corresponding to grades 1-3 (from the early stage to the advanced stage of osteoarthritis) according to the ICRS classification of cartilage defect. Therefore, the agent of the present invention can be used for treating or preventing the diseases classified into the early stage to the advanced stage of osteoarthritis.

Table 2 shows the Kellgren-Lawrence classification (hereinafter also referred to as "KL classification") of osteoarthritis.

TABLE 2

Kellgren-Lawrence classification

| Grade 0 | Normal (no bone spur, no narrowed joint cleft) |
|---|---|
| Grade 1 | Suspected microscopic bone spur formation |
| | No narrowed joint cleft |
| Grade 2 | Mild osteoarthritis |
| | Microscopic bone spur formation |
| | Narrowed joint cleft (more than ½ of remaining joint cleft) |
| Grade 3 | Moderate osteoarthritis |
| | Bone spur formation |
| | Narrowed joint cleft (less than ½ of remaining joint cleft) |
| Grade 4 | Severe osteoarthritis |
| | Large bone spur formation |
| | Prominent narrowed joint cleft |
| | (with some closed joint cleft) |

According to the KL classification, osteoarthritis is classified into grades 0-4. In the KR classification, grade 0 is the stage where osteoarthritis has yet to develop. Grade 1 is the early stage of osteoarthritis. Grades 2-3 are the advanced stages of osteoarthritis. Grade 4 is the late stage of osteoarthritis. In the KR classification, narrowing of joint cleft is derived from cartilage degeneration such as extinction of cartilage cells. As mentioned above, the targets of the agent of the present invention are the diseases classified into the early stage to the advanced stage of osteoarthritis. That is, the targets of the agent of the present invention are the diseases classified into any one of grades 1-3 under the KL classification of osteoarthritis. In Table 2, Grades 0-4 of the KL classification are equivalent to Grades 0-4, respectively, of the ICRS classification.

Table 3 shows the Outerbridge classification (hereinafter also referred to as "OB classification") of osteoarthritis.

TABLE 3

Outerbridge classification

| Grade 0 | Normal |
|---|---|
| Grade 1 | Softening and ridge of cartilage |
| Grade 2 | Crack in part of the surface layer not reaching subchondral bone or having a diameter of about 1.5 cm |
| Grade 3 | Crack with a diameter of more than 1.5 cm reaching subchondral bone |
| Grade 4 | Exposed subchondral bone |

According to the OB classification, osteoarthritis is classified into grades 0-4. In the OB classification, grade 0 is the stage where osteoarthritis has yet to develop. Grade 1 is the early stage of osteoarthritis. Grades 2-3 are the advanced stages of osteoarthritis. Grade 4 is the late stage of osteoarthritis. In the KR classification, narrowing of joint cleft is derived from cartilage degeneration such as extinction of cartilage cells. As mentioned above, the targets of the agent of the present invention are the diseases classified into the early stage to the advanced stage of osteoarthritis. That is, the targets of the agent of the present invention are the diseases classified into any one of grades 1-3 under the OB classification of osteoarthritis. In Table 2, Grades 0-4 of the KL classification are equivalent to Grades 0-4, respectively, of the OB classification.

Table 4 shows the classification by the modified Mankin score of osteoarthritis.

TABLE 4

Modified Mankin score

Safranine O-fast green staining

| Score 0 | Homogeneously stained everywhere in cartilage joint |
|---|---|
| Score 1 | Deletion of staining in the surface layer at about less than ½ of a plateau state |
| Score 2 | Deletion of staining in the surface layer at about more than ½ of a plateau state |
| Score 3 | Deletion of staining in the surface layer and the inner layer at about less than ½ of a plateau state |
| Score 4 | Deletion of staining in the surface layer and the inner layer at about more than ½ of a plateau state |
| Score 5 | Deletion of staining in all three layers at about less than ½ of a plateau state |
| Score 6 | Deletion of staining in all three layers at about more than ½ of a plateau state |

Cartilage cell defect

| Score 0 | No cell decrease |
|---|---|
| Score 1 | Slight cell decrease |
| Score 2 | Moderate cell decrease |
| Score 3 | Remarkable cell decrease |
| Score 4 | Decrease in virtually all cells |

Structure

| Score 0 | Normal |
|---|---|
| Score 1 | Abnormal in the surface |
| Score 2 | 1-3 surface cracks |
| Score 3 | More than 4 surface cracks |
| Score 4 | 1-3 cracks extended to the inner layer |
| Score 5 | More than 4 cracks extended to the inner layer |
| Score 6 | 1-3 cracks extended to the deep layer |
| Score 7 | 4 cracks extended to the deep layer |
| Score 8 | Crack(s) extended to the calcified layer |

Figure 4:
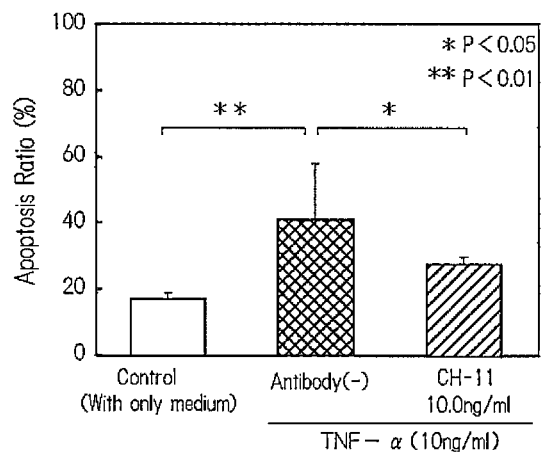
FIG. 4 is a graph replaced with a drawing showing the apoptosis suppression effect of an anti-Fas IgM antibody.

In the safranine O-fast green staining of the modified Mankin score, osteoarthritis is classified depending on the degree of staining at the time of staining articular cartilage tissue. In cartilage cell defect, osteoarthritis is classified depending on the stained cartilage cell mass. And in structure, osteoarthritis is classified depending on the degree of crack (s) appearing in articular cartilage. In FIG. 4, scores 1-3 are the early stages of osteoarthritis corresponding to Grade 1 of the ICRS classification. Scores 4-5 are the advanced stages of osteoarthritis corresponding to Grade 2 of the ICRS classification. Scores 6-8 are also the advanced stages of osteoarthritis corresponding to Grade 3 of the ICRS classification. As mentioned above, the targets of the agent of the present invention are the diseases classified into the early stage to the advanced stage of osteoarthritis. That is, the targets of the agent of the present invention are the diseases classified into any one of scores 1-7 under the modified Mankin classification of osteoarthritis.

As demonstrated in the examples described below, an anti-Fas IgM antibody can control the condition (cartilage degeneration) of osteoarthritis with scores 2-7 of the modified Mankin score. Furthermore, as demonstrated in the examples descried below, an anti-Fas IgM antibody can control cartilage matrix defect. Moreover, an anti-Fas IgM antibody can improve the ability to produce cartilage matrix. As mentioned above, the Mankin scores 2-7 are the early stages to the advanced stages of osteoarthritis accompanied with cartilage degeneration as its pathological condition. Therefore, an anti-Fas IgM antibody can be used effectively as a treatment agent or preventive agent for the diseases classified into the early stages to the advanced stages of osteoarthritis.

As demonstrated in the examples described below, an anti-Fas IgM antibody can control the condition (cartilage degeneration) of osteoarthritis with scores 2-7 of the modified Mankin score. Furthermore, as demonstrated in the examples descried below, an anti-Fas IgM antibody can control cartilage matrix defect. Moreover, an anti-Fas IgM antibody can improve the ability to produce cartilage matrix. As mentioned above, the Mankin scores 2-7 are the early stages to the advanced stages of osteoarthritis accompanied with cartilage degeneration as its pathological condition. Therefore, an anti-Fas IgM antibody can be used effectively as a treatment agent or preventive agent for the diseases classified into the early stages to the advanced stages of osteoarthritis.

The drug of the present invention can act as a treatment agent or preventive agent for arthritis derived from osteoarthritis, containing an anti-Fas IgM antibody as an active ingredient. Arthritis derived from osteoarthritis is a secondary inflammatory response derived from osteoarthritis. In osteoarthritis, disruption of the surface articular cartilage, accompanying proliferation of new cartilage at the joint periphery, joint degeneration, etc. stimulate peripheral cells and cause a secondary inflammatory response. The agent of the present invention can preferably be used as a treatment agent or preventive agent of such arthritis derived from osteoarthritis.

Furthermore, the agent of the present invention can be used as an inhibitory agent against cartilage matrix degeneration, a cartilage matrix synthesis improving agent, and an apoptosis inducing agent against macrophage induced by osteoarthritis, containing an anti-Fas IgM antibody as an active ingredient. The anti-Fas IgM antibody is preferably CH11 or 7C11. As demonstrated in the examples described below, such an anti-Fas IgM antibody can effectively be used as an inhibitory agent against cartilage matrix degeneration, a cartilage matrix synthesis improving agent, and an apoptosis inducing agent against macrophage induced by osteoarthritis.

In this specification, an antibody is protein induced into the living body. Examples of such a living thing are mammals and birds. Example of the antibody of the present invention is an anti-Fas antibody derived from mammals, such as human, mouse, and rat. The antibody of the present invention can be used as drugs for animals such as dog or cat as well as human. In order to avoid side effects after administration, the antibody is preferably derived from the living thing to which the antibody is to be administered. Examples of the antibody types administered to humans are a mouse antibody, a chimeric antibody, a humanized antibody, and (complete) human antibody.

Such an antibody can be manufactured by a well-known method (for example, Tadaomi Takenawa, "Protein Experiment Handbook", Yodosha Co., Ltd., 2003, p. 86-p. 105). An immunized animal which produces an antibody is injected with protein or peptide which is an antigen to which the antibody binds. A well-known animal used as an immunized animal such as a mouse, a rat, a hamster, a rabbit, and a goat can be used as an immunized animal. The immunized animal is injected with the antigen once or more than twice periodically (for example, every 2-4 weeks). After injection of the antigen, blood is collected periodically (for example, every 1-2 weeks), and the production of the target antibody (antibody titer) is checked. A well-known method can be used as a method for checking an antibody titer, such as Western Blotting and ELISA. An antibody derived from an immunized animal (e.g. a mouse antibody for a mouse) can be obtained by such a method.

A chimeric antibody is an antibody consisting of the variable region of a mouse antibody connected to the constant region of a human antibody, which can be manufactured by a well-known method (fore example, Kokai (unexamined patent publication) No. H7-194384). A humanized antibody is an antibody wherein the complementarity determining region (CDR) of a mouse antibody is transplanted into the variable region of a human antibody, which can be manufactured by a well-known method (U.S. Pat. No. 2,828,340, Kokai (unexamined patent publication) No. H11-4694, etc.). A human antibody is an antibody produced by the introduction of a human immunoglobulin gene to the knockout animal with the destroyed immunoglobulin gene which an immunized animal inherently has, which can be manufactured by a well-known method (Kokai (unexamined patent publication) No. H10-146194, Kokai (unexamined patent publication) No. H10-155492, etc.). A complete human antibody is an antibody produced by human cells, which can be manufactured by a well-known method (Kokai (unexamined patent publication) No. 2007-141, Kokai (unexamined patent publication) No. 2005-34154, etc.). A person skilled in the art can appropriately choose any of these well-known methods for manufacturing an antibody to manufacture the antibody of the present invention A Fas antigen is transmembrane glycoprotein, also referred to as APO-1, CD95, ALPS1A, APT1, Fas1, FasL receptor, TNF receptor super family member 6 (TNF receptor superfamily member 6), TNFR6, etc. A Fas antigen developing on the cell surface is known to act as a receptor inducing apoptosis in the cells (Fas-mediated apoptosis) through stimulation of Fas ligand (FasL), anti-Fas antibody, etc. A Fas antigen is widely distributed in the cells constituting each tissue within the living body. Furthermore, a Fas antigen also develops in macrophages, natural killer (NK) cells, B cells, T cells, and inflammation-related cells such as granular leukocytes and monocytes. A FasL is reported to develop in T cells, NK cells, effector cells, etc. A Fas antigen, if it binds to a Fas ligand or an anti-Fas antibody, forms a trimer. Furthermore, the trimerized intracellular domain of a Fas antigen is known to transmit apoptosis signals into the cells. In addition, a Fas ligand is known to form a trimer within the living body, and it is thought that binding of the trimerized Fas ligand to a Fas antigen causes trimerization of intracellular domain of the Fas antigen, resulting in transmission of apoptosis signals.

An anti-Fas antibody includes a Fas-mediated apoptosis inducing antibody (agonist antibody), a Fas-mediated apoptosis inhibiting antibody (antagonistic antibody), etc. A preferable anti-Fas antibody of the present invention is a Fas-mediated apoptosis inducing antibody (agonist antibody). Such an anti-Fas antibody includes an antibody against a peptide consisting of an amino acid sequence which is the same as an amino acid sequence described in SEQ ID NO: 1 or an amino acid sequence where 1-10 amino acid residues are replaced, deleted, added, or inserted, for example. SEQ ID NO: 1 is an amino acid sequence showing a human Fas antigen. Among the amino acid sequence depicted in SEQ ID NO: 1, the number of the amino acid residues replaced, deleted, added, or inserted is 1-10, for example, preferably 1-5, more preferably 1-2, still more preferably 1. The agent of the present invention comprising an anti-Fas antibody can also target animals such as a dog and a cat in addition to humans. When the agent of the present invention comprising an anti-Fas antibody is used as a drug for animal, the anti-Fas antibody is preferably an antibody against a peptide consisting of an amino acid sequence which is the same as an amino acid sequence described in SEQ ID NO: 1 showing a Fas antigen derived from humans or an amino acid sequence where its 1-10 amino acid residues are replaced, deleted, added, or inserted rather than an antibody against a peptide consisting of an amino acid sequence which is the same as an amino acid sequence constituting a Fas antigen derived from the administered animal or an amino acid sequence where its 1-10 amino acid residues are replaced, deleted, added, or inserted. The amino acid sequence constituting this kind of animal-derived Fas antigen may be obtained using a well-known site such as GenBank.

In a preferred aspect of the present invention, an anti-Fas antibody is an antibody recognizing the extracellular domain of a Fas antigen. Specifically, the anti-Fas antibody is an antibody against a peptide consisting of an amino acid sequence which is the same as an amino acid sequence depicted in amino acids 26-173 of SEQ ID NO: 1, or an amino acid sequence where its 1-5 amino acid residues are replaced, deleted, added, or inserted. Among the amino acid sequence depicted in amino acids 26-173 of SEQ ID NO: 1, the number of the amino acid residues replaced, deleted, added, or inserted is 1-15, for example, preferably 1-2, more preferably 1. An example of these amino acid residues replaced etc. is described in UniProt (the universal protein resource accession No: P25445. The amino acid sequence depicted in amino acids 26-173 of SEQ ID NO: 1 is a sequence showing the extracellular domain of a Fas antigen. A preferred Fas antibody of the present invention is a Fas-mediated apoptosis inducing antibody. That is, the Fas antibody of the present invention is preferably an antibody which may bind to a Fas antigen, cause trimerization of the Fas antigen, transmit apoptosis signals into the cells. By making the anti-Fas antibody of the present invention an antibody against the extracellular domain of a Fas antigen, when the agent comprising the anti-Fas antibody is administered, it can preferably bind to a Fas antigen, cause its trimerization, and promote intracellular signal transmission.

The anti-Fas antibody of the present invention may be a polyclonal antibody or may be a monoclonal antibody. However, a polyclonal antibody is hard to have a stable antibody titer. Therefore, a monoclonal antibody with a stable antibody titer is more preferable. Although Isotypes of an antibody (immunoglobulin (Ig) molecule) include IgG, IgM, IgA, IgE, and IgD, the antibody of the present invention is preferably an IgG antibody, an IgA antibody, or an IgM antibody, more preferably an IgA antibody or an IgM antibody, still more preferably an IgM antibody. These antibodies can be manufactured by the method described below (but not limited thereto) as well as a well-known manufacturing method.

An antibody (immunoglobulin (Ig) molecule) has the basic structures common to each isotype (IgG, IgM, IgA, IgE, IgD), and consists of an H chain (Heavy chain) with a molecular weight of 50,000-70,000, and an L chain (Light chain) with a molecular weight of 20,000-25,000. And the H chain has characteristic structures for every isotype, which are called γ chain, μ chain, α chain, δ chain, and ε chain, corresponding to IgG, IgM, IgA, IgD, and IgE, respectively. Also, there are known two types of the L chain, L and K, which are called λ chain and κ chain, respectively. In the basic structure—peptide chain structure—, two H chains and two L chains which are homologous to each other are bound by a disulfide bond (S—S bond) and a noncovalent bond. The two types of L chain can be paired with any types of H chain. For example, in case of IgM, the combination of μ chain, λ chain, and κ chain is $\mu_2\lambda_2$ and $\mu_2\kappa_2$. There are four intrachain disulfide bonds in an H chain (five in case of μ chain and ε chain) while there are two intrachain disulfide bonds in an L chain, and one loop is formed for every amino acid residues 100-110, and the unit is called domain. The H chain and the L chain have domains called variable (V) regions (denoted by $V_H$ and $V_L$, respectively) located in the N-terminal domain. And the amino acid sequences located closer to the C-terminal than the N-terminal have domains called constant (C) regions (denoted by $C_H1$, $C_H2$, $C_H3$, $C_L$) having almost constant amino acid sequences for each isotype. The antigen-binding site (epitope) an antibody consists of $V_H$ and $V_L$, and the antigen specificity varies with the sequence of this site. And such an antibody forms different polymerized structures depending on the isotypes. For example, while the IgM antibody is an antibody consisting of two Hp chains and two L chains, it exists in the form of a pentamer or a hexamer bound with an additional polypeptide called J chain. While the IgA antibody is an antibody consisting of two Hα chains and two L chains, it exists in the forms of a monomer, a dimer, or a trimer. And the dimer or the trimer of the IgA antibody is bound by a J chain or a secretory piece. The IgG antibody exists in the form of a monomer. Any type of these antibodies can be used for the anti-Fas antibody of the present invention. Furthermore, as mentioned above, in Fas-mediated apoptosis, binding of a trimeric Fas ligand to a Fas antigen promotes the trimerization of intracellular domain of the Fas antigen, resulting in transmission of apoptosis signals. As mentioned above, as the IgM antibody forms a polymerized structure (pentamer or hexamer), the IgM antibody binds to hold more than three Fas antigens. This effectively causes the trimerization of a Fas antigen, resulting in transmission of apoptosis signals. Thus, from this point of view, it is preferable to use an IgM antibody for the anti-Fas antibody of the present invention.

[Polyclonal Antibody]

An example of a method for manufacturing a polyclonal antibody is shown below. However, it can be changed suitably using a well-known method for a person skilled in the art. A polyclonal antibody can be prepared by injecting an antigen (immunogen) into the immunized animal mentioned above. As an antigen (immunogen) injected into the immunized animal, an antigen expression cell, (crude) purified protein, recombinant protein, or a synthetic peptide can be used. Such an antigen includes a peptide consisting of an amino acid sequence which is the same as an amino acid sequence described in SEQ ID NO: 1 described above or an amino acid sequence where its 1-10 amino acid residues are replaced, deleted, added, or inserted. As mentioned below, as the anti-Fas antibody of the present invention is an antibody which induce Fas-mediated apoptosis, the antigen is preferably a peptide consisting of an amino acid sequence which is the same as an amino acid sequence described in amino acids 26-173 of SEQ ID NO: 1 described above or an amino acid sequence where its 1-5 amino acid residues are replaced, deleted, added, or inserted, and the number of amino acid residues replaced with, deleted from, added to or inserted into the above amino acid sequence is more preferably 1-2, still more preferably 1. Furthermore, as the anti-Fas antibody of the present invention is an antibody which binds to a Fas antigen and induces Fas-mediated apoptosis, as a peptide (antigen) used in manufacturing an antibody, a shorter peptide may be used than a peptide consisting of an amino acid sequence depicted in amino acids 26-173 of SEQ ID NO: 1. A person skilled in the art can suitably adjust the length of a peptide.

In manufacturing a polyclonal antibody, an antigen is mixed with adjuvant to be injected into an immunized animal. As used herein, adjuvant refers to a substance used to strengthen the immune response to an antigen, which includes, for example, aluminum adjuvant, incomplete Freund's adjuvant, and *Bordetella pertussis* adjuvant. Injection of antigens into the immunized animal is performed every 2-4 weeks. Subsequent to more than twice injection, blood collection is performed 1-2 weeks after injection, and then an antibody titer check is performed. The injection dose and the number of injection (number of immunization) to an immunized animal vary from the type of the immunized animal or each individual. A person skilled in the art can adjust suitably them according to the result of the antibody titer check. After immunization, whole blood is squeezed out, from which serum is separated using a well-known method such as centrifugal separation. Serum is refined so as to remove endogenous antibodies contained in serum. As the refinement method, a well-known method such as affinity chromatography can be used. Thus a polyclonal antibody can be prepared.

[Antigen-Presenting Cell]

An antigen-presenting cell used as an antigen is preferably a cell on whose cell membrane antigen protein is expressed (e.g. a cultured cell). Such an antigen-presenting cell can be prepared by a well-known method. Specifically, a DNA coding antigen protein may be introduced into the cultured cell to be expressed. The cultured cell (hereinafter also referred to as "host") presenting an antigen is not particularly limited; a well-known cell may be used, such as a B cell or a dendritic cell known as a antigen-presenting cell. As a method for presenting antigen protein on these cells, an antigen expression vector into which DNA coding antigen protein is incorporated may be prepared and be introduced into the cell presenting the antigen. In case DNA incorporated into the expression vector does not contain a cell membrane domain sequence, the cell membrane domain sequence the host into which the expression vector is introduced has may be contained. Containing this kind of sequence can effectively present protein (antigen) on the cell membrane. A person skilled in the art can suitably obtain this kind of cell membrane domain sequence to be contained in the DNA sequence incorporated in the expression vector. As this kind of expression vector, a promoter, an enhancer, a splicing signal, a poly A signal, a selective marker, substance containing SV40 origin of replication, etc. can be used. When the host is an animal cell, the promoter can be a SRα promoter, a SV40 promoter, a HIV-LTR promoter, a CMV promoter, a HSV-TK promoter, for example. The selective marker can be a dihydrofolate reductase gene (Methotrexate (MTX) resistance), an ampicillin resistance gene, a neomycin resistance gene (G418 resistance), a hydromycin resistance gene, a blasticidin resistance gene, etc., for example. As this kind of expression vector, a well-known expression vector may be used, which a person skilled in the art can choose suitably depending on the host. As a method for introducing an antigen expression vector, a well-known method such as a calcium phosphate method, a lipofection method, and an electroporation method can be used. As a method for checking whether an antigen is expressed in a cell, a well-known method such as an immunostaining method may suitably be used. The cell where an antigen is expressed can be collected by a well-known method and be used as an antigen to be injected into an immunized animal.

[(Crude) Purified Protein]

The (crude) purified protein is prepared by purifying protein which a cultured cell etc. express. This kind of protein may be expressed by stimulating a cultured cell etc. with a drug or factor acting on the signaling pathway of cells or acting on a transcriptional factor. The expressed protein can be purified by a well-known method and be used as purified protein. For example, secreted protein, with its supernatant collected, can be purified by salting-out, column chromatography, membrane processing, etc. Chromatography can be ion-exchange chromatography, gel filtration chromatography, affinity chromatography, hydrophobic chromatography, etc., which a person skilled in the art can use suitably according to the nature of protein. Protein not secreted out of cell can be collected by collecting the cultured cells and breaking the same by ultrasonic treatment etc. Protein may then be purified by the above-mentioned methods. These kinds of methods for obtaining purified protein are well-known, which a person skilled in the art can use suitably depending on the nature of protein.

[Recombinant Protein]

Recombinant protein used as an antigen can be prepared by a well-known method. Specifically, DNA coding recombinant protein used as an antigen is inserted into a vector by a well-known method, and is introduced to the host expressing the recombinant protein. Well-known vectors can be used, which a person skilled in the art can choose depending on the introduced host. As this kind of host, a well known host such as bacteria, an insect cell, a plant cell, and an animal cell can be used. And as the method for introducing a vector to a host, a well-known method such as an electroporation method, a calcium phosphate method, and the lipofection method can be used depending on the host. Recombinant protein may be fusion protein with a tag such as GST (glutathion S transferase), HA (hemagglutinin), or (oligo) histidine. These tags may be bound at the N-terminal or the C-terminal of DNA coding the target antigen. This kind of tag-bound fusion protein can purify expressed protein easily. The protein expressed on the host can be collected, for example, by collecting the culture supernatant in case of secreted protein, otherwise by breaking the host cell with ultrasonic treatment etc. As a method for purifying protein, HPLC, an affinity column, etc. can be used, for example. Furthermore, recombinant protein can be obtained using an in vitro protein expression system or a living body such as an inset, an animal, a plant, etc. These methods are well-known, to which a person skilled in the art can suitably make any changes.

[Synthetic Peptide]

A method for synthesizing peptide includes a solid phase method, a liquid phase method, etc. Peptide synthesis includes a stepwise extension method for binding the target amino acid sequences sequentially from the N-terminal or the C-terminal, or a fragment condensation method for breaking the amino acid sequences into appropriate fragments and condensing these fragments to synthesize the target peptide. Furthermore, a method for synthesizing peptide includes a solid phase method for binding amino acids with insoluble resin whereon the amino acids are bound one by one based on the amino acid sequence information whereby the chain is extended or a liquid phase method not using a carrier such as resin. Moreover, peptide can be synthesized effectively by combining these methods. These kinds of methods are well-known, which a person skilled in the art can use suitably to synthesize the target amino acid sequences. In addition, synthesized peptide may be purified. Purification of synthetic peptide can be done using a well-known method such as a precipitation method, HPLC, ion-exchange chromatography, and gel filtration chromatography. When synthetic peptide is used as an antigen, as it lacks antigenicity as it is, it is better used covalently bonded to a carrier such as BSA (Bovine Serum Albumin) or KLH (Keyhole Limpet Hemocyanin) with a cross linking agent (such as MBS (m-maleimidobenxoic acid) ester or DMS (dimethyl suberimidate).

[Monoclonal Antibody]

A monoclonal antibody can be manufactured by a well-known method.

Specifically, the above-mentioned antigen is injected (immunized) into an immunized animal (e.g. a mouse) at intervals of 2-4 weeks for 1-6 months, and an antibody titer check is performed as in the case of a method for manufacturing a polyclonal antibody. Once a desired antibody titer is obtained by the check, the spleen is isolated from the immunized animal. The isolated spleen is suspended in a serum-free medium (e.g. Iscove's medium) to prepare a spleen cell suspension. Spleen cells and myeloma cells are mixed to be fused together with polyethylene glycol (PEG). Thereafter, by culturing in a hypoxanthine-aminopterine-thymidine (HAT) selection medium, only a hybridoma (cell consisting of fused spleen cells and myeloma cells) is allowed to grow. Furthermore, in order to choose the hybridoma producing the target antibody, simultaneously with the check for the target antibody, cloning of a check-positive hybridoma is performed. Repeating this procedure several times can provide a cloned hybridoma producing the target antibody. Thereafter, injecting the cloned hybridoma into the peritoneal cavity of the immunized animal, collecting ascites after 2-4 weeks, and purifying the ascites can provide a monoclonal antibody. As a method for purifying ascites, a well-known method such as affinity chromatography or gel filtration chromatography can be used.

[Method for Manufacturing Recombinant Antibody]

Moreover, the antibody of the present invention may be a recombinant antibody. A recombinant antibody is a recombinant monoclonal antibody not using a hybridoma in the antibody production processes. An example of a hybridoma includes one having only minimal antigen-binding sites, one having polyvalent antigen-binding sites, secreted type one consisting of a combination of IgG and IgA, a chimera of xenogeneic animals, or humanized one. These recombinant antibodies can be obtained by making immunoglobulin of each isotype express on the host. Examples of a production system using this kind of host include a method using coliform *bacillus*, a method using cultured cells, a method of causing a plant to produce, a method of causing a transgenic mouse to produce, etc.

These recombinant antibodies may be manufactured using a well-known method. A specific example is the phage display method (e.g. recombinant antibody expression system (Amersham Biosciences)). The phage display method is a system for causing foreign genes to express as fusion protein on the coat protein of fibrous phage such as M13, one of coliform *bacillus* viruses, so that the infectious ability of phage may not be lost. Phage is a virus infected with bacteria, and if a foreign gene is incorporated into the DNA, it gains the ability to invade the host at the time of infection and grow.

[Phage Display Method]

Although one example of a method for manufacturing a monoclonal antibody by the phage display method is shown below, the present invention is not limited to the following manufacturing method, and a person skilled in the art can change each step suitably using other well-known methods. Furthermore, a person skilled in the art can set parameters such as temperature, reaction time, solution concentration of use, and amount of solution of use in each step and make any changes to implement the method. In the phage display method, at first a phage antibody library is prepared, and then screening for antibody production phage is performed to prepare a monoclonal antibody.

Preparation of Phage Antibody Library (1) Extract mRNA from B Cell and Perform RT-PCR to Prepare a cDNA Library The cells extracted from a mouse, a human, etc. may be used for B-cell. The extraction of RNA from B-cell can be done using, for example, the AGPC method (the Acid-Guanidinium-Phenol-Chloroform method) etc. In the AGPC method, at first guanidine thiocynate solution is added to B-cell to homogenize. Then, sodium acetate, phenol, and chloroform are added to the homogenized solution of the cells to mix and centrifuge. After centrifugation, the aqueous layer of the solution is collected. Isopropanol is added to the collected aqueous layer, mixed, and centrifuged to precipitate RNA. The precipitation (RNA) is again dissolved with guanidine thiocynate solution, and then shaken with sodium acetate, phenol, and chloroform added. After shake, the aqueous layer is centrifuged and again collected. Isopropanol is again added to the collected aqueous layer and centrifuged to precipitate RNA. 70% ethanol is added to the precipitated RNA, suspended, and again centrifuged to precipitate RNA, resulting in total RNA. Next, with regard to the extraction of mRNA from total RNA, mRNA is amplified by PCR using a primer (oligo dT primer) binding to poly-A sequence existing at the C-terminal of mRNA, which can be extracted/purified with a oligo dT column (e.g. manufactured by QIAGEN). Alternatively, mRNA may be extracted/purified with affinity chromatography using magnetic beads (e.g. manufactured by Nacalai Tesque, Inc.) coated with oligo dT. The purified mRNA can prepare a cDNA library by PCR in the reaction solution containing reverse transcriptase.

(2) Amplify the Variable Regions of an L Chain (Light Chain) and an H Chain (Heavy Chain), Respectively, by PCR Using Specific Primers.

The sequences of $V_H$ and $V_L$, variable regions of an H chain and an L chain of an antibody (immunoglobulin (Ig) molecule), can be obtained from GenBank etc., for example. In order to obtain an IgA human antibody, for example, the $V_H$ and $V_L$ sequences of human IgA should be obtained, the primer design for increasing these sequences should be done, and the both sequences should be amplified by PCR using the above-mentioned cDNA as a template. A person skilled in the art can do the primer design suitably depending on the antibody to be obtained and can decide the conditions of PCR etc. suitably. The amplified $V_L$ and $V_H$ may be purified by a well-known method.

(3) Construction of a Library

The purified $V_L$ and $V_H$ are connected by a linker to be a single-chain, which is inserted into a phagemid vector to construct a single-chain (variable region (variable region fragment) gene library. A linker is a sequence for connecting each fragment. As this kind of linker, a well-known linker may be used. A phagemid vector is a plasmid vector incorporating a replication origin (IG region) required for the production of single-chain DNA of M13 phage or f1 phage. The phagemid vector has the characteristic as a plasmid and the characteristic of a single-chain DNA phage, which can be manipulated as a general double-chain DNA plasmid, and also can cause fibrous phage particles containing one DNA chain of the plasmid to produce. A well-known phagemid vector (e.g. pCANTAB5E (Amersham Biosciences)) may be used. Otherwise, antibody gene fragments may be amplified by PCR using a primer specific to the Fd section of an antibody H chain ($V_H$ and $C_H1$ regions) and the L chain section, and these gene fragments may be inserted into a phagemid vector to construct a gene library corresponding to an antibody Fab.

Screening for Antibody Production Phage (4) Concentration of an Antibody-Presenting Phage Library An antibody-presenting phage library is prepared by introducing a antibody gene library constructed using a phagemid vector to coliform *bacillus* and infecting helper phage (e.g. M13KO7, VCSM13). One method for concentrating this phage library is the punning method. Though this method, the phage group presenting the target antibody can be concentrated by a solid phase method using the purified antigen (antigen purified by the above-mentioned method). In the punning method, the steps of the reaction between a solid-phased antigen and a phage library, washing (removal of a phage library not bound to a solid-phased antigen), elution of an antigen-binding phage, amplification by infection to coliform *bacillus* are repeated several times (e.g. 4-5 times). This can concentrate the antigen-specific phage (antibody production phage).

(5) Selection of an Antigen-Specific Phage Clone and Acquisition of a Monoclonal Antibody As a selection method of an antigen-specific phage clone, the ELISA method etc. can be used, for example. An antibody production phage is reacted with the ELISA plate coated with the purified antigen, and the reactivity (binding character) with the purified antigen is checked. By repeating this step and selecting clones, phages producing monoclonal antibodies can be obtained. And, by allowing these phages to grow in coliform *bacillus* and collecting antibodies, monoclonal antibodies can be obtained. These antibodies can be purified using a well-known purification method such as affinity chromatography.

A preferred embodiment of the present invention includes a use of the antibody of the present invention for manufacturing a treatment agent or preventive agent for osteoarthritis and arthritis (arthromeningitis) derived from osteoarthritis, an inhibitory agent against cartilage matrix degeneration, a cartilage matrix production agent, and an apoptosis inducing agent against macrophage induced by osteoarthritis. That is, the present invention provides: a method for treating osteoarthritis; a method for treating arthritis derived from osteoarthritis; a use of an anti-Fas IgM antibody for manufacturing an inhibitory agent against cartilage matrix degrading enzyme production; and a use of an anti-Fas IgM antibody for manufacturing an apoptosis inducing agent against macrophage induced by osteoarthritis. And in the use of this anti-Fas IgM antibody, each pattern explained earlier can be used in combination.

The agent of the present invention may be manufactured by a well-known method to a person skilled in the art. Although the agent of the present invention can be manufactured as an oral preparation and a parenteral preparation, the latter is more preferable. This kind of parenteral preparation may be liquid medicine (such as aqueous liquid medicine, non-aqueous liquid medicine, suspended liquid medicine, and emulsified liquid medicine), or may be solid medicine (such as powder filling preparation and freeze-dried preparation). Alternatively, the agent of the present invention may be a sustained preparation.

Liquid medicine can be manufactured by a well-known method. For example, liquid medicine can be manufactured by dissolving antibodies in a pharmaceutically acceptable solvent and filling the sterilized container for liquid medicine. A pharmaceutically acceptable solvent may be an injection solvent, distilled water, physiological saline, an electrolyte solution agent, etc., for example, and it is preferable to use sterilized solvents. A sterilized container for liquid medicine may be an ampule, a vial, a bag, etc. A well-known container of glass or plastic can be used for these containers. A specific container of plastic may be one made of material such as polyvinyl chloride, polyethylene, polypropylene, ethylene, and vinyl acetate copolymer. A sterilization method of these containers or solvents may be a heating method (e.g. a flame method, a drying method, a high-temperature steam method, a free-flowing steam method, and a boiling method), a filtration method, an irradiation method (e.g. a radiation method, an ultraviolet method, and a high-frequency method), a gas method, a medical fluid method, etc. A person skilled in the art can choose and select suitably any of these sterilization methods depending on the material of a container or the property of a solvent.

As a method for manufacturing solid medicine, a well-known method such as a freeze-drying method, a spray drying method, and a sterile recrystallization method can be used. For example, a freeze-dried preparation can be manufactured through the following steps: (1) place the crystallized antibodies at room temperature of 4° C. and under ordinary pressure for 2-3 hours to cool (cooling step); (2) place at room temperature of −50° C. and under ordinary pressure for 12-15 hours to freeze (freezing step); (3) place at room temperature of −20° C. and under ordinary pressure for 4-6 hours to recrystallize (recrystallizing step); (4) place at room temperature of −50° C. and under ordinary pressure for 14-16 hours to refreeze (refreezing step); (5) place at room temperature of −13° C. and under the pressure of 10-20 kPa (under high vacuum) for 24-26 hours (first drying step); (6) place at room temperature of 24° C. and under the pressure of 10-20 kPa (under high vacuum) for 10-121 hours (second drying step); (7) place at room temperature of 24° C. and under ordinary pressure. Thus, the freeze-drying method freezes at low temperature and sublimes fluid (ice) to be removed. Although the freeze-dried preparation of the present invention can be manufactured by, but not limited to, the above-mentioned method, a person skilled in the art can make any changes suitably. Also, any arbitrary changes to parameters such as temperature, pressure, time, etc. in each step can be made.

Furthermore, the present invention can also provide a kit product with a combination of the agent containing an anti-Fas IgM antibody of the present invention and a medical device. For example, the agent containing an anti-Fas IgM antibody of the present invention may be filled into a medical device such as a syringe. Alternatively, solid medicine may be filled into one side of a soft bag while solvent may be filled into the other side through a separate wall, and they may be mixed together by opening up the separate wall when used. These can not only alleviate healthcare professional's burdens for preparation at the point of use but also prevent bacterial contamination, invasion of foreign objects, resulting in preferred use of them. Healthcare professionals can use suitably such a syringe or a soft bag as they are well-known.

The agent containing an anti-Fas IgM antibody of the present invention can be administered with a well-known method such as intravenous administration, intraarterial administration, intramuscular administration, subcutaneous administration, intraperitoneal administration, and intranarial administration. Administration by injection is preferable, and instillation is also available. Furthermore, the agent of the present invention may be directly injected into the affected area (e.g. joint) or may be administered by opening the affected area by surgery. Although the agent of the present invention can be prepared as an oral formulation and a parenteral formulation, a parenteral formulation is more preferable. This kind of parenteral formulation may be liquid medicine (aqueous liquid medicine, non-aqueous liquid medicine, suspended liquid medicine, emulsified liquid medicine, etc.) or may be solid medicine (powder filling formulation, freeze-dried formulation, etc.). Solid medicine, when administered, is used dissolved in use or suspended with pharmaceutically administered solvent at the desired concentration. This kind of solid medicine can be used by an administration method such as injection or instillation.

When the agent containing an anti-Fas IgM antibody of the present invention is formulated, it also can be formulated in combination with a pharmaceutically acceptable carrier or medium etc. where necessary. In addition, the agent may contain a drug. Furthermore, the agent containing an anti-Fas IgM antibody of the present invention may contain protein which inhibits the antibody action of the present invention, such as albumin, lipoprotein, and globulin. Including such protein can improve the stability of antibodies contained in liquid medicine. In case the agent of the present invention is formulated as liquid medicine, such protein may be contained in the liquid medicine. In case the agent of the present invention is formulated as solid medicine, the above-mentioned protein may be contained when the anti-Fas antibody of the present invention is solidified or may be contained in the liquid medicine where the solid medicine is dissolved. The content of such protein is 0.01-5 pts·wt on the assumption that the liquid measure at the time of administration is 100 pts·wt, and a person skilled in the art can suitably adjust the content depending on the amount of administered antibodies or other substances contained.

[Pharmaceutically Acceptable Carrier or Medium]

A pharmaceutically acceptable carrier or medium may include an excipient, a stabilizer, a solubilizing agent, an emulsifier, a suspending agent, a buffering agent, a tonicity agent, an anti-oxidization agent, or a preserving agent, for example. Alternatively, a high-polymer material such as polyethylene glycol (PEG) or a conjugate compound such as cyclodextrin may be used. Although specific examples of carriers or media are given below, the present invention is not limited thereto; well-known ones can be used. Starch or lactose etc. not having pharmacological effects per se are preferable as an excipient. A stabilizer may include albumin, gelatin, sorbitol, mannitol, lactose, sucrose, trehalose, maltose, glucose, etc. Among these, lactose or trehalose is preferable. A solubilizing agent may include ethanol, glycerin, propylene glycol, polyethylene glycol, etc. An emulsifier may include lecithin, aluminium stearate, or sorbitan sesquioleate etc. A suspending agent may include macrogol, poly vinyl pyrrolidone (PVP), or carmellose (CMC). A tonicity agent may inclue sodium chloride, glucose, etc. A buffering agent may include citric salt, acetate, boric acid, or phosphate etc. An anti-oxidization agent may include ascorbic acid, sodium hydrogen sulfite, sodium pyrosulfite, etc. A preserving agent may include phenol, a thimerosal, a benzalkonium chloride, etc.

A medicine combined with the antibody of the present invention may include a well-known medicine used for articular diseases, such as a treatment agent for articular disease, an anti-inflammatory agent, an analgesic, a bone regeneration agent, an osteoclastic inhibitor, an antibiotic, or a growth agent, etc. Furthermore, a soothing agent may be contained because there may be pain due to injection when the agent containing an anti-Fas antibody of the present invention is administered by injection. One or more of these medicines may be combined.

A treatment agent for articular disease may include articular cartilage extracellular matrix degradation inhibitor (WO 2004/017996), a protecting agent of articular cartilage such as adrenal corticosteroid, chondoitin sodium sulfate, or hyaluronic acid (HA), or p21-activated kinase (PAK) inhibitor (Kohyo (national publication of translated version) No. 2007-537134), etc.

An anti-inflammatory agent may include a steroidal anti-inflammatory agent or a non-steroid anti-inflammatory agent (NSAIDs), etc. A steroidal anti-inflammatory agent may include dexamethasone, cortisone, hydrocortisone, prednisolone, methylprednisolone, betamethasone, triamcinolone, triamcinolone acetonide, fluocinolone acetonide, fluocinonide, and beclomethasone, and ethenezamide etc. A non-steroid anti-inflammatory agent may include aspirin, ibuprofen, naproxen, diclofenac, indomethacin, nabtomen, phenylbutazone, rofecoxib, celecoxib, oxicam, piroxicam, pyrazolone, azapropazone, etc., for example.

An analgesic may include an opioid analgetic etc. in addition to an antiphlogistic analgesic NSAIDs. An opioid analgetic may include endorphin, dynorphine, enkephalin, codeine, dihydrocodeine, dextropropoxyphene, etc., for example.

An osteoclastic inhibitor may be any one or more mixtures of an estrogen agent, calcitonin, and bisphosphonate.

An antibiotic may include a penicillin antibiotic, a cephem antibiotic, an aminoglycoside antibiotic, a macrolide antibiotic, a tetracycline antibiotic, and a peptide antibiotic, etc. A penicillin antibiotic may include benzylpenicillin, phenoxymethyl penicillin, methicillin, flucloxacillin, amoxicillin, ampicillin, piperacillin, azlocillin, ticarcillin, etc. A cephem antibiotic may include cefazolin, cefuroxime, cefamandole, cefotaxime, cefoperazone, cefpiramide, cephalexin, cefaclor, cefixime, cefteram, etc. An aminoglycoside antibiotic may include gentamicin, netilmicin, tobramycin, streptomycin, neomycin, kanamycin, amikacin, etc. A macrolide antibiotic may include erythromycin, clarithromycin, roxithromycin, rokitamycin, clindamycin, azithromycin, etc. A tetracycline antibiotic may include tetracycline, minocycline, toxicycline, etc. In addition, a β-lactam antibiotic may include latamoxef, flomoxef, azthreonam, imipenem, and panipenem. In addition, other antibiotic may include vancomycin, rifampicin, chloramphenicol, etc.

A growth agent may include a bone morphogenetic protein (BMP), a bone growth factor (BGF), and a platelet-derived growth factor (PDGF), a basic fibroblast growth factor (bFGF), an insulin, an insulin-like growth factor (IGF), hormone, cytokine, or a transforming growth factor (TGF) etc. One or more of these growth agents may be contained, and they may also be combined with other well-known medicinal medicine.

Different medicines are used as a soothing agent depending on whether the pain by injection is attributed to the ph and osmotic pressure of liquid medicine significantly different from those of body fluid or the pain is caused by the action of the medicine itself. In case the pain is attributed to the differences in the ph and osmotic pressure, liquid medicine containing a buffering agent, a tonicity agent, etc. is preferable. On the other hand, the pain is caused by the action of the medicine itself, topical anesthetic etc. are suitable for use. A well-known medicine such as benzyl alcohol, chlorobutanol, procaine hydrochloride, lidocaine hydrochloride, dibucaine hydrochloride, mepivacaine hydrochloride, etc., for example, may be used as topical anesthetic.

The agent containing an anti-Fas IgM antibody of the present invention manufactured as above as an active ingredient can be used as a treatment method or preventive method for administering effective amount to the patient with osteoarthritis and arthritis derived from osteoarthritis. Furthermore, the agent containing an anti-Fas IgM antibody of the present invention as an active ingredient can be used as a treatment method or preventive method to inhibit cartilage matrix degrading enzyme production, to promote or improve cartilage matrix production, and to induce apoptosis induction agent against macrophage induced by osteoarthritis. That is, the present invention provides: a method for treating arthritis derived from osteoarthritis which administering an effective amount of anti-Fas IgM antibodies to the target; a method for inhibiting cartilage matrix degrading enzyme production which administering an effective amount of anti-Fas IgM antibodies to the target; a method for producing cartilage matrix which administering an effective amount of anti-Fas IgM antibodies to the target; a method for inducing apoptosis induction agent against macrophage induced by osteoarthritis. And the respective patterns explained earlier can be used in combination in the use of these anti-Fas IgM antibodies.

The agent of the present invention is used as an injection, a drug in an injection device. A well-known method may be used as a non-limiting administering method of the drug of the present invention. Examples may include intravenous injection, artery injection, subcutaneous injection, intramuscular injection, instillation, etc. Furthermore, the agent of the present invention may be injected directly to the affected area (e.g. joint), or may be administered with the affected area open by surgery. A person skilled in the art can suitably choose the administering method suitable for the patient. An effective amount of the anti-Fas IgM antibodies—the main ingredient of the agent of the present invention—may be contained in the agent of the present invention. Supposing that the total weight is 100 pts·wt., the rate of the anti-Fas IgM antibodies of the present invention may be $1 \times 10^{-3}$-$1 \times 10$ pts·wt., preferably $1 \times 10^{-2}$-$1 \times 10^{-1}$ pts·wt., more preferably $5 \times 10^{-2}$-$5 \times 10^{-1}$ pts·wt. The administration amount varies with the subjects, ages, symptoms, etc. to be administered. Generally, the daily administration amount is 1 ng-100 μg of an active ingredient of the antibodies per individual, preferably 10 ng-10 μg, more preferably 100 ng-1 μg. Otherwise, the daily administration amount is 10 pg-2 μg per weight of 1 kg, preferably 100 pg-200 μg, more preferably 1 pg-20 μg. It is preferred to administer the daily administration amount in 2-5 doses. Moreover, the number of doses a day can be reduced by preparing the agent of the present invention as a sustained preparation. A well-known method can be used in preparing such a sustained preparation. Administering in several doses or preparing a sustained preparation makes it easy to keep the concentration of the drug constant, resulting in persistent medicinal effect as well as reduced adverse effects, which can reduce the burden on the patient.

Hereinafter, although the present invention is explained based on specific examples, the present invention is not limited to these examples.

EXAMPLE 1

Establishment of Cultured Cells

After informed consent was gotten, osteocartilaginous tissues and peripheral blood were extracted from the surgical tissues of the patient with osteoarthritis, and the synovial fibroblasts, the cartilage cells, and the macrophage were extracted by the following method.

Synovial Fibroblast

After informed consent was gotten, synovial tissues were extracted from the surgical tissues of the patient with osteoarthritis, which were chopped and were processed overnight in the liquid low glucose Dulbecco's modified Eagle's medium (DMEM, manufactured by Gibco) culture medium (37° C.) containing 1.0 mg/ml collagenase (collagenase), and the cultured synovial fibroblasts were separated. The cells were usually cultured in a cultivation flask (a cultivation area of 25 cm$^2$), and when used in an experiment, the cells were cultured in the culture dish of polyethylene (a diameter of 6 cm). Cell culture was performed using the DMEM culture medium with an addition of inactivation fetal bovine serum (Fetal Bovine Serum (FBS), Heat-inactivated, manufactured by TRACE) by 10% of the medium content as well as 2 mM L-glutamine, 25 mM HEPES, 100 units/ml penicillin and streptomycin, in the $CO_2$ incubator (normal oxygen concentration environment) set to 37° C., saturated humidity, 5% $CO_2$+95% air. As for the cell passage, the cells were washed with the phosphate buffering solution (PBS, manufactured by Nissui), exfoliated with 0.25% trypsin-PBS solution (manufactured by Gibco), dispersed by pipetting, and diluted to a suitable concentration in the medium.

Cartilage Cell

After informed consent was gotten, cartilage tissues were extracted from the surgical tissues of the patient with osteoarthritis, which were chopped and were processed overnight in the liquid low glucose Dulbecco's modified Eagle's medium (DMEM, manufactured by Gibco) culture medium (37° C.) containing 1.5 mg/ml collagenase B (collagenase B), and the cultured cartilage cells were separated. The cells were usually cultured in a cultivation flask (a cultivation area of 25 cm$^2$), and when used in an experiment, the cells were cultured in the culture dish of polyethylene (a diameter of 6 cm). Cell culture was performed using the DMEM culture medium with an addition of inactivation fetal bovine serum ((FBS, manufactured by TRACE) by 10% of the medium content as well as 2 mM L-glutamine, 25 mM HEPES, 100 units/ml penicillin and streptomycin, in the $CO_2$ incubator (normal oxygen concentration environment) set to 37° C., saturated humidity, 5% $CO_2$+95% air. As for the cell passage, the cells were washed with the phosphate buffering solution (PBS, manufactured by Nissui), exfoliated with 0.25% trypsin-PBS solution (manufactured by Gibco), dispersed by pipetting, and diluted to a suitable concentration in the medium.

Macrophage

After informed consent is gotten, 50 ml blood was collected from the patient whose surgical donation was extracted as mentioned above to obtain 1% heparinized blood. The centrifuging tube where this blood is arranged in a multilayered way was centrifugated for 30 minutes at 1500 rpm, and the lymphocyte and the macrophage were separated. Cell culture was performed using the RPMI culture medium with an addition of inactivation fetal bovine serum (FBS, manufactured by TRACE) by 10% of the medium content as well as 2 mM L-glutamine, 25 mM HEPES, 100 units/ml penicillin and streptomycin, in the $CO_2$ incubator (normal oxygen concentration environment) set to 37° C., saturated humidity, 5% $CO_2$+95% air.

Cell Culture Using a Two-Layer Transwell Chamber

Synovial fibroblasts ($1 \times 10^6$/well) or macrophages ($1 \times 10^6$/well) were disseminated to the upper part and cartilage cells ($1 \times 10^6$/well) were disseminated to the lower part both of the two-layer transwell chamber (Toyobo) separated with a porosity filter with size of 3 μm, and were cultured. The upper layer (inflammatory cell culture layer) of this culture system is equivalent to synovitis while the lower layer (cartilage culture layer) is equivalent to cartilage tissue. Anti-Fas IgM antibodies of various concentration (0.1, 1.0, 10.0 ng/ml) were added to the upper layer of the chamber or inflammatory cytokines (TNF-α: 10 ng/ml or IL-1β:10 ng/ml) were added to the upper layer under the conditions of non-addition, and were cultured for 48 hours. The culture supernatant and cells were temporally collected, and various cell activities were analyzed by the following experiment methods.

EXAMPLE 2

Examination of the Inhibitory Action of the Cartilage Matrix Degrading Enzyme (MMP) Production by Anti-Fas IgM Antibodies The effect of anti-Fas IgM antibodies (CH11 (mouse antibody) (manufactured by MBL)) on cartilage matrix degrading enzyme production enhanced by cartilage catabolic inducing factor TNF-α was analyzed using the enzyme-linked immunosorbent assay (ELISA). The anti-Fas IgM antibodies (CH-11) used in the examination were antibodies produced from the hybridoma obtained by the fusion of mouse myeloma cells NS-1 and the spleen of a Balb/c mouse. The hybridoma was prepared from the antibodies derived from the human diploid fibroblast cell line FS-7.

The cartilage cells separated/cultured by the above-mentioned method were disseminated to the lower layer of the transwell chamber and synovial fibroblasts were disseminated to the upper layer both at a density of $1 \times 10^6$ well. TNF-α (10 ng/ml) was added to the upper layer. In addition, anti-Fas IgM antibodies of various concentration (0.1, 1.0, 5.0, 10.0 ng/ml) or hyaluronan preparation (HA) were added to the upper layer in combination as indicated by the following Table 5, cultured for 48 hours, and the culture solution was collected. Also, hyaluronan preparation (HA) was used as control. The combination of examination conditions was shown in the following Table 5. In Table 5, TNF-α concentration of TNF-α (+) is 10 ng/ml. The concentration unit of HA is mg/ml, and the concentration unit of anti-Fas IgM antibodies CH-11 is ng/ml. No. 1 of the table is negative control, and No. 2 is positive control.

TABLE 5

| | No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| TNF-α | − | + | + | + | + | + | + | + | + | + | + | + |
| HA | — | — | 0.1 | 1.0 | — | — | — | — | 1.0 | 1.0 | 1.0 | 1.0 |
| CH-11 | — | — | — | — | 0.1 | 1.0 | 5.0 | 10.0 | 0.1 | 1.0 | 5.0 | 10.0 |

The concentrations of cartilage matrix degrading enzyme matrix metalloproteinase (MMP)-1 and MMP-3 in the culture supernatant were determined using the ELISA kit (MMP-1, MMP-3: manufactured by R&D) which is a standard technology currently known in the art. The ELISA was performed by the following standard method. The ELISA was performed with example number 6 (n=6). The diluted culture supernatant sample of 100 μl per sensitization plate 1 well was added, and placed statically for one hour at a room temperature (primary reaction). After the primary reaction, each well was fully washed more than 4 times using a washing bottle by PBS. The horseradish peroxidase (HRP) labeled goat anti-rabbit IgG (H+L) antibodies diluted with 0.1% Tween20-PBS up to 3000 times were injected to each well separately by 100 μl, and were placed statically for one hour at a room temperature (secondary reaction). After the secondary reaction, each well was similarly washed by PBS, where 0.8 mM TMB (tetramethylbenzidine) solution was added by 1000 per well, and color formed for 5-20 minutes at 30° C. (color forming reaction). The color forming reaction was halted by adding 1.5N $H_3PO_4$ by 100 μl per well, and the absorbance at 450 nm was measure using a microtiter plate reader. The measurement concentration was calibrated using a control freeze-drying reagent in accordance with the instruction provided by the manufacturer, and the test of significant differences was performed. In the figure, "*" indicates that the reject rate (P value) of the test of significant differences is less than 0.05 (P<0.05), and "**" indicates that the reject rate (P value) of the test of significant differences is less than 0.01 (P<0.01) (it is the same hereafter).

FIG. 2A is a graph replaced with a drawing showing how an anti-Fas IgM antibody influences the ability to produce MMP1. The vertical axis of FIG. 2A shows MMP1 produced from the cartilage cells in a concentration per 1 ml of culture media. According to the result, the control ability to cartilage matrix degrading enzyme (MMP1) production enhanced by TNF-α was higher in anti-Fas IgM antibodies (Nos. 5-8) than in single HA (Nos. 3 and 4). Thus, anti-Fas IgM antibodies have shown to be able to control effectively MMP1 production.

FIG. 2B is a graph replaced with a drawing showing how an anti-Fas IgM antibody influences the ability to produce MMP3. The vertical axis of FIG. 2B shows MMP3 produced from the cartilage cells in a concentration per 1 ml of culture media. According to the result, the control ability to cartilage matrix degrading enzyme (MMP3) production enhanced by TNF-α was higher in anti-Fas IgM antibodies (Nos. 5-8) than in single HA (Nos. 3 and 4). Thus, anti-Fas IgM antibodies have shown to be able to control effectively MMP3 production.

In FIG. 2, anti-Fas IgM antibodies have shown to control effectively cartilage matrix degrading enzyme MMP production. As mentioned above, MMP degrades articular cartilage. Therefore, MMP may be the cause of inducing osteoarthritis or worsening condition of osteoarthritis. As shown in the present example, an anti-Fas IgM antibody can control MMP production. Thus, an anti-Fas IgM antibody can control the induction of osteoarthritis, and can control worsening of the condition of osteoarthritis. Therefore, an anti-Fas IgM antibody can be used suitably as a preventive agent of osteoarthritis. Furthermore, as MMP1 and MMP3 are also involved in the immune response, an anti-Fas IgM antibody can also be used as a preventive agent or treatment agent for arthritis derived from osteoarthritis induced after osteoarthritis by controlling MMP1 and MMP3 production.

EXAMPLE 3

Examination of Improvement Effect of Anti-Fas IgM Antibodies on the Decreased Cartilage Matrix Production Ability The control effect of anti-Fas IgM antibodies on the decreased cartilage matrix (proteoglycan) production ability by cartilage catabolic inducing factor TNF-α or IL-1β was analyzed using ELISA.

In the same way as used in the above "Examination of the inhibitory action of the cartilage matrix degrading enzyme (MMP) production by anti-Fas IgM antibodies", the cartilage cells were disseminated to the lower layer of the transwell chamber and synovial fibroblasts were disseminated to the upper layer both at a density of $1 \times 10^6$ well. TNF-α (10 ng/ml) or IL-1β (10 ng/ml) was added to the upper layer. In addition, anti-Fas IgM antibodies of various concentration (0.1, 1.0, 5.0, 10.0 ng/ml) or hyaluronan preparation (HA) were added to the upper layer or cultured for 48 hours under the condition of non-addition, and the culture solution was collected. Cartilage matrixes in the culture supernatant were determined using the ELISA kit (proteoglycan: manufactured by Biosource) which is a standard technology currently known in the art. The result is shown in FIG. 3.

FIG. 3 is a graph replaced with a drawing showing the effect of an anti-Fas IgM antibody on the reduced ability to produce cartilage matrix (proteoglycan). In FIG. 3, the vertical axis shows the production amount of proteoglycan. The higher vertical axis values show more production amount of proteoglycan. That is, this shows that anti-Fas IgM antibodies improved the ability to produce proteoglycan controlled by TNF-α. As a result, anti-Fas IgM antibodies have shown to be able to improve improved the ability to produce proteoglycan controlled by TNF-α and IL-1β.

In FIG. 3, an anti-Fas IgM antibody has shown to improve the synthesis of a cartilage matrix (proteoglycan). In osteoarthritis, destruction of articular cartilage as a pathological condition is observed. Therefore, as an anti-Fas IgM antibody can improve synthesis of a cartilage matrix (proteoglycan)

required for reproduction of the articular cartilage destroyed in osteoarthritis, it can be used suitably as a treatment agent of osteoarthritis.

EXAMPLE 4

Inhibitory Effect of an Anti-Fas IgM Antibody on Apoptosis

The inhibitory effect of an anti-Fas IgM antibody on apoptosis of cartilage cells induced by cartilage catabolic inducting factor TNF-α was examined using Apo Stand ELISA Apotosis Detection Kit (Biomol International). This is a kit capable of detecting apoptosis quantitatively by denaturing specifically DNA of apoptotic cells by formamide and detecting denatured DNA by an anti-single-stranded DNA antibody.

In the same way as used in the above "Examination of the inhibitory action of the cartilage matrix degrading enzyme (MMP) production by anti-Fas IgM antibodies", the cartilage cells were disseminated to the lower layer of the transwell chamber and marcophages were disseminated to the upper layer both at a density of $1 \times 10^6$ well. TNF-α (10.0 ng/ml) was added to the upper layer. In addition, anti-Fas IgM antibodies (10.0 ng/ml) were added to the upper layer or cultured for 48 hours under the condition of non-addition. The medium/inducing substances were removed, the attached cell fixation solution was added to the kit, and the cells were fixed. Thereafter, the solution was removed/dried, formamide was added, heated at 56° C., and the DNA of apoptotic cells was heat denatured. After cooling, formamide was removed, and a blocking solution was added for blocking. The blocking solution was removed, an anti-single-stranded DNA (ssDNA) antibody was added, and the antibody was cultured for 4 hours at a room temperature. After washing three times by PBS, the absorbance at 405 nm was measured with a microtiter plate leader. The result is shown in FIG. 4.

FIG. 4 is a graph replaced with a drawing showing the apoptosis suppression effect of an anti-Fas IgM antibody. In FIG. 4, the vertical axis shows the rate (%) of apoptosis of the cell nucleus. That is, a lower value shows that apoptosis was controlled more, As a result, an anti-Fas IgM antibody has shown to be control apoptosis of cartilage cells caused by TNF-α. In osteoarthritis, TNF-α is known to be in induced condition. Therefore, the present example has shown that an anti-Fas IgM antibody can control apoptosis of cartilage cells caused by osteoarthritis.

In FIG. 4, an anti-Fas IgM antibody has shown to control the death of cartilage cells by a macrophage. Therefore, an IgM type anti-Fas antibody is considered to control cartilage degeneration, and thus it can preferably be used preferably as a treatment agent or preventive agent of osteoarthritis. Moreover, it is contemplated that these actions occurred because an anti-Fas IgM antibody induced apoptosis of a macrophage. A macrophage is known to induce inflammatory cytokine. Therefore, an anti-Fas IgM antibody controls the release of inflammatory cytokine and an inflammatory reaction by inducing apoptosis of a macrophage. Thus, an anti-Fas IgM antibody can be used as a treatment agent or preventive agent to the secondary inflammatory reaction (arthritis derived from osteoarthritis) induced by osteoarthritis.

EXAMPLE 5

With regard to the potential as an OA therapeutic drug of an agonist anti-Fas antibody with apoptosis induction ability, the difference in the potential derived from the difference in isotype (IgG or IgM) of an antibody was evaluated in an in vitro experiment system. UB2 (manufacture by MBL) and ZB4 (manufacture by MBL) were used as an IgG antibody. CH-11 (manufactured by MBL) and 7C11 (manufacture by Beckman Coulter) were used as an IgM antibody. An IgG isotype control (manufactured by SouthernBiotech) and an IgM isotype control (manufactured by SouthernBiotech) were used as each control.

Establishment of Cultured Cells

After informed consent was gotten, osteocartilaginous tissues and peripheral blood were extracted from the surgical tissues of the five patients (n=5) with osteoarthritis, and the synovial fibroblasts, the cartilage cells, and the macrophage were extracted by the same method as that in Example 1.

Cell Culture Using a Two-Layer Transwell Chamber

Synovial fibroblasts ($1 \times 10^5$/well) or macrophages ($1 \times 10^5$/well) were disseminated to the upper part and cartilage cells ($1 \times 10^5$/well) were disseminated to the lower part both of the two-layer transwell chamber (Toyobo) separated with a porosity filter with size of 3 μm, and were cultured. The upper layer (inflammatory cell culture layer) of this culture system is equivalent to synovitis while the lower layer (cartilage culture layer) is equivalent to cartilage tissue. Anti-Fas IgM antibodies of various concentration or an isotype control were added to the upper layer of the chamber or inflammatory cytokines (TNF-α: 10 ng/ml) were added to the upper layer under the conditions of non-addition, and were cultured for 48 hours. The culture supernatant and cells were temporally collected, and various cell activities were analyzed by the following experiment methods.

Inhibitory Action of the Cartilage Matrix Degrading Enzyme (MMP) Production by Anti-Fas IgM Antibodies of Each Isotype The effect of anti-Fas IgM antibodies of each isotype on cartilage matrix degrading enzyme production enhanced by cartilage catabolic inducing factor TNF-α was analyzed using the enzyme-linked immunosorbent assay (ELISA).

The cartilage cells separated/cultured by the above-mentioned method were disseminated to the lower layer of the transwell chamber and synovial fibroblasts were disseminated to the upper layer both at a density of $1 \times 10^5$ well. TNF-α (10 ng/ml) was added to the upper layer. In addition, anti-Fas IgM antibodies of various concentration (0.01 nm) were added to the upper layer, or cultured for 48 hours under the condition of non-addition, and the culture solution was collected.

The concentrations of cartilage matrix degrading enzyme matrix metalloproteinase (MMP)-1 and MMP-3 in the culture supernatant were determined using the ELISA kit (MMP-1, MMP-3: manufactured by R&D) which is a standard technology currently known in the art. The ELISA was performed in the same way as mentioned above. The result is shown FIG. 5.

FIG. 5A is a graph replaced with a graph showing how an anti-Fas IgM antibody or an anti-Fas IgG antibody influences the ability to produce MMP1 of cartilage cells. The vertical axis of FIG. 5A shows MMP1 produced from the cartilage cells in a concentration per 1 ml of culture media. No. 1 in FIG. 5A shows a negative control, and No. 2 shows a positive control. As a result, the control ability to cartilage matrix degrading enzyme (MMP1) production enhanced by TNF-α was higher in anti-Fas IgM antibodies (Nos. 7-8) than in anti-Fas IgG antibodies (Nos. 5-6). Thus, it is contemplated that anti-Fas IgM antibodies can control effectively MMP1 production.

FIG. 5B is a graph replaced with a graph showing how an anti-Fas IgM antibody or an anti-Fas IgG antibody influences the ability to produce MMP3 of cartilage cells. The vertical axis of FIG. 5b shows MMP3 produced from the cartilage cells in a concentration per 1 ml of culture media. No. 1 in FIG. 5B shows a negative control, and No. 2 shows a positive control. As a result, the control ability to cartilage matrix degrading enzyme (MMP3) production enhanced by TNF-α was higher in anti-Fas IgM antibodies (Nos. 7-8) than in anti-Fas IgG antibodies (Nos. 5-6). Thus, it is contemplated that anti-Fas IgM antibodies can control effectively MMP3 production.

In FIG. 5, anti-Fas IgM antibodies have shown to control effectively cartilage matrix degrading enzyme MMP production. As mentioned above, MMP degrades articular cartilage. Therefore, MMP may be the cause of inducing osteoarthritis or worsening condition of osteoarthritis. As shown in the present example, an anti-Fas IgM antibody can control MMP production. Thus, an anti-Fas IgM antibody can control the induction of osteoarthritis, and can control worsening of the condition of osteoarthritis. Therefore, an anti-Fas IgM antibody can be used suitably as a preventive agent of osteoarthritis. Furthermore, as MMP1 and MMP3 are also involved in the immune response, an anti-Fas IgM antibody can also be used as a preventive agent or treatment agent for arthritis derived from osteoarthritis induced after osteoarthritis by controlling MMP1 and MMP3 production.

EXAMPLE 6

Inhibitory Effect of an Anti-Fas IgM of Each Isotype Antibody on Apoptosis

The inhibitory effect of an anti-Fas IgM antibody of each isotype on apoptosis of cartilage cells induced by cartilage catabolic inducting factor TNF-α was examined using Apo-Stand ELISA Apotosis Detection Kit (Biomol International).

In the same way as mentioned above, the cartilage cells were disseminated to the lower layer of the transwell chamber and marcophages were disseminated to the upper layer both at a density of $1 \times 10^5$ well. TNF-α (10 ng/ml) was added to the upper layer. In addition, anti-Fas IgM antibodies (0.01 nM) were added to the upper layer or cultured for 48 hours under the condition of non-addition. The medium/inducing substances were removed, the attached cell fixation solution was added to the kit, and the cells were fixed. Thereafter, the solution was removed/dried, formamide was added, heated at 56° C., and the DNA of apoptotic cells was heat denatured. After cooling, formamide was removed, and a blocking solution was added for blocking. The blocking solution was removed, an anti-single-stranded DNA (ssDNA) antibody was added, and the antibody was cultured for 4 hours at a room temperature. After washing three times by PBS, the absorbance at 405 nm was measured with a microtiter plate leader. The result is shown in FIG. 6.

In FIG. 6, an anti-Fas IgM antibody has shown to control the death of cartilage cells by a macrophage. Therefore, an IgM type anti-Fas antibody is considered to control cartilage degeneration, and thus it can preferably be used preferably as a treatment agent or preventive agent of osteoarthritis. Moreover, it is contemplated that these actions occurred because an anti-Fas IgM antibody induced apoptosis of a macrophage. A macrophage is known to induce inflammatory cytokine. Therefore, an anti-Fas IgM antibody controls the release of inflammatory cytokine and an inflammatory reaction by inducing apoptosis of a macrophage. Thus, an anti-Fas IgM antibody can be used as a treatment agent or preventive agent to the secondary inflammatory reaction (arthritis derived from osteoarthritis) induced by osteoarthritis.

In FIG. 6, an anti-Fas IgM antibody has shown to control the death of cartilage cells by a macrophage. Therefore, an IgM type anti-Fas antibody is considered to control cartilage degeneration, and thus it can preferably be used preferably as a treatment agent or preventive agent of osteoarthritis. Moreover, it is contemplated that these actions occurred because an anti-Fas IgM antibody induced apoptosis of a macrophage. A macrophage is known to induce inflammatory cytokine. Therefore, an anti-Fas IgM antibody controls the release of inflammatory cytokine and an inflammatory reaction by inducing apoptosis of a macrophage. Thus, an anti-Fas IgM antibody can be used as a treatment agent or preventive agent to the secondary inflammatory reaction (arthritis derived from osteoarthritis) induced by osteoarthritis.

EXAMPLE 7

Effect of an Anti-Fas IgM Antibody on an Osteoarthritis Model Rat

A medicinal effect evaluation test of an anti-Fas IgM antibody CH-11 was performed using rats inducing osteoarthritis.

Preparation of a Osteoarthritis Model Rat

After rats (Wister rat, weights 200 g-250 g) were quarantined and habituated/bred for about one week, the hair at a knee joint portion of the left foot was removed by combined anesthesia of Ketamine hydrochloride (Pfizer, Inc., Ketalar 100) and xylazine hydrochrolide (intramuscular administration), or in case of poor anesthetic effect by intravenous administration of the said combined anesthetic solution or pentobarbital Na, and then was disinfected with an iodine system antibacterial Isodine. After disinfection, the outer skin inside the knee joint was cut open, a tibial collateral ligament was cut, and an articular capsule was checked/cut open to expose/remove the entire medial meniscus. Then, the circumference tissues and outer skin of the articular capsule were sutured. At the suture, the surgical site was washed with physiological saline (500 mg (factor)/20 ml) containing an antibiotic (ampicillin sodium for injection)

The prepared osteoarthritis model rats were divided into the subgroup as shown in the following Table 6, and they were provided with test articles or target solutions by intraarticular injection once per week over 24 weeks using 27 gauge syringes.

TABLE 6

| Experiment group | | treatment | Numbers of autopsy per 4 weeks | Total number |
|---|---|---|---|---|
| A | Control | Arthritis operation + saline (medium) | — | 5 |
| B | Non-specific antibody control | Arthritis operation + IgM antibody administration | 5 | 30 |
| C | Test article at a low dose | Arthritis operation + low dose of CH-11 | 5 | 30 |
| D | Test article at a high dose | Arthritis operation + high dose of CH-11 | 5 | 30 |
| E | Surgical control | Sham operation + saline (medium) | — | 2 |

Pathological Inspection

Five rats per every 4 week were euthanized by phlebotomy deep anesthesia of pentobarbital Na (intravenous administration), and then autopsy was performed. As to 8th, 12th, and 24th week planned autopsy examples, right and left knee joint tissues, heart, lung, liver, spleen, kidney, brain, spermary, and seminal vesicle were extracted fixed with 4% paraformaldehyde solution. Joint tissues were decalcified with the Planck- Rychlo decalcification solution and neutralized, and then hematoxylin-eosin staining and safranine O staining were performed for paraffin-embedded and chopped specimen. As for other organs, hematoxylin-eosin staining and safranine O staining were performed for paraffin-embedded and chopped specimen, and the histopathological test with an optical microscope was carried out.

Influence on the Arthrosis Pathology Tissue Score by Administration of Anti-Fas IgM Antibodies The prepared osteoarthritis model rats were divided into three groups, and 50.0 μl of saline or control antibody solution (10.0 ng/ml) was injected to the left knee joint of the control group (A and B in FIG. 3) and 50.0 μl of CH-11 (low-dose administration group: 1.0 ng/ml, high-dose administration group: 10.0 ng/ml) was injected to the left knee joint of CH-11 administration group (C and d in FIG. 3) once a week using a micro-needle injection syringe. Example number 4 (N=4) was used in each group. The disease condition of arthritis and arthrosis (arthrosis pathological tissue score) was observed in the 4th week, the 8th week, the 12th week, the 16th week, and 24 weeks after disposal, and the differences between two groups were compared statistically with the Student's T method. In both group, the right knee joint was non-treated, and the degree of advance and progress of arthrosis was observed comparatively. The result is shown in FIG. 7. The Modified Mankin score shown in the above FIG. 4 was used as the arthrosis pathological tissue score.

FIG. 7A shows the result of Safranine O staining. FIG. 7B shows the result of cartilage cell defect. FIG. 7C shows the result of cartilage structure. The vertical axis in FIGS. 7A-7C shows each score, and the horizontal axis shows the variation over hour. As a result of FIGS. 7A-7C, the degree of cartilage degeneration (modified Mankin score) of the knee joint of rats in the control group was observed to be enhanced over time, and the induction and aggravation (transition from an initial stage to an advanced stage of osteoarthritis) of arthrosis were confirmed. On the other hand, the score of the CH-11 administration group tends to show a low value compared to the average score of the control group from the 8th week after the start of administration, and after the 12th week, the statistically significant differences were seen both in the CH11 lose-dose administration group and CH-11 high-dose administration group. Thus, the anti-Fas IgM antibody CH-11 has shown to control cartilage degeneration in the osteoarthritis rats at initial to advanced stages. Therefore, an anti-Fas IgM antibody has shown to used effectively for the treatment of the diseases classified into the initial to advanced stages of osteoarthritis accompanied with cartilage degeneration.

EXAMPLE 8

Influence on the Pathological Tissues by Administering Anti-Fas IgM Antibodies

The influence on each tissue when anti-Fas IgM antibodies were administered to the osteoarthritis rats was examined by the above-mentioned histopathological inspection. The arthritis model rats of the 12th week and the 24th weeks after disposal were used as the osteoarthritis model rats. The observed and photographed pathological specimens of the knee joint tissues of each rat with an optical microscope were shown in FIGS. 8 and 9. In FIGS. 8 and 9, "×40" and "×200" indicate the magnification of the optical microscope.

FIG. 8 are photographs replaced with drawings showing the histopathological specimens of osteoarthritis model rats in 12 weeks after treatment. FIGS. 8A-8F show the histopathological specimens of osteoarthritis model rats of control. FIGS. 8G-8J show the histopathological specimens of osteoarthritis rats of a CH-11 low-dose administration group (CH-11: dose of 1.0 ng/ml). FIGS. 8K-8N show the histopathological specimens of osteoarthritis rats of show the histopathological specimens of osteoarthritis model rats of a CH-11 high-dose administration group (CH-11: dose of 10.0 ng/ml). FIG. 8O shows the histopathological specimen of an osteoarthritis model rat of control. FIG. 8P shows the histopathological specimen of an osteoarthritis model rat of a CH-11 low-dose administration group (CH-11: dose of 1.0 ng/ml). FIG. 8B, FIG. 8D, FIG. 8F, FIG. 8I, FIG. 8K, and FIG. 8M are enlarged photographs replaced with drawings of portions surrounded by a square of FIG. 8A, FIG. 8C, FIG. 8E, FIG. 8H, FIG. 8J, FIG. 8L, and FIG. 8N, respectively.

From the result of FIG. 8, cartilage degeneration (clustering of cartilage cells and disappearance of cartilage cells) was confirmed in the control group (FIGS. 8A-8F, and 8O) as compared to the CH-11 administration group (FIGS. 8G-8N, and 8P). The clustering of cartilage cells can be determined from the increase in the staining portion by Safranine O. And the disappearance of cartilage cells can be determined from the decreased stainability of safranine O (SO) as shown in FIGS. 8O and 8P. This result shows that as administration of CH-11 can control cartilage degeneration, CH-11 can treat or prevent osteoarthritis accompanied by cartilage degeneration.

FIG. 9 are photographs replaced with drawings showing the histopathological specimens of osteoarthritis model rats in 24 weeks after treatment. FIGS. 9A-9H show the histopathological specimens of osteoarthritis model rats of control. FIGS. 9I-9L show the histopathological specimens of osteoarthritis rats of a CH-11 low-dose administration group (CH-11: dose of 1.0 ng/ml). FIGS. 9M-9P show the histopathological specimens of osteoarthritis rats of show the histopathological specimens of osteoarthritis model rats of a CH-11 high-dose administration group (CH-11: dose of 10.0 ng/ml). FIG. 9B, FIG. 9D, FIG. 9F, FIG. 9H, FIG. 9I, FIG. 9K, FIG. 9M, and FIG. 9O are enlarged photographs replaced with drawings of portions surrounded by a square of FIG. 9A, FIG. 9C, FIG. 9E, FIG. 9G, FIG. 9J, FIG. 9L, FIG. 9N, and FIG. 9P, respectively.

From the result of FIG. 9, cartilage degeneration (disappearance of cartilage cells and structure degeneration of cartilage matrixes) was confirmed in the control group (FIGS. 9A-9H) as compared to the CH-11 administration group (FIGS. 9I-9P). This shows that as administration of CH-11 can control cartilage degeneration, CH-11 can treat or prevent the diseases classified into the initial to advanced stages of osteoarthritis accompanied with cartilage degeneration.

Furthermore, in the present osteoarthritis model rats, the CH-11 intra-articular administration group was observed to significantly control a secondary synovitis (inflammation) and cartilage degeneration as compared to the control rat group. Furthermore, the bone proliferative change (bone spur) which was observed in the control rat in the later stage of a test was hardly observed in the CH-11 intra-articular administration group. As to internal organs other than knee joint (heart, lung, liver, spleen, kidney, brain, spermary, and seminal vesicle), there was not be found particular histological differences between the control group and the CH-11 administration group. Therefore, it turned out that an anti-Fas IgM antibody can specifically control the diseases classified into the initial to advanced stages of osteoarthritis accompanied with cartilage degeneration also in an animal.

INDUSTRIAL APPLICABILITY

The treatment agent or preventive agent of the present invention may be used in the pharmaceutical industry.

The invention claimed is:

1. A method of treating patient who suffers from osteoarthritis, comprises
   administering to the patient an agent containing an anti-F as IgM antibody as an active ingredient and a pharmaceutically acceptable carrier by means of injection,
   wherein the osteoarthritis classified as any of grade 1 to 3 according to the ICRS classification, any of grade 1 to 3 according to the Kellgren-Lawrence classification, or any of grade 1 to 3 according to the Outerbridge classification, and
   wherein the anti-F as IgM antibody is an agonist antibody against the extracellular domain of a Fas antigen, and wherein the anti-F as IgM antibody is the only active ingredient.

2. The method as claimed in claim 1,
   wherein the anti-Fas IgM antibody is CH11 or 7C11.

3. A method of treating a patient who suffers from cartilage destruction associated with osteoarthritis, comprises
   administering to the patient an agent comprising an inhibitory agent against cartilage destruction containing an anti-Fas IgM antibody as an active ingredient and a pharmaceutically acceptable carrier by means of injection,
   wherein the anti-Fas IgM antibody is an agonist antibody against the extracellular domain of a Fas antigen, and wherein the anti-Fas IgM antibody is the only active ingredient, and
   wherein the patient having a disease classified as any of grade 1 to 3 according to the ICRS classification of osteoarthritis.

4. The method as claimed in claim 3,
   wherein the anti-Fas IgM antibody is CH11 or 7C11.

5. A method of treating a patient who suffers from cartilage matrix degeneration associated with osteoarthritis, comprises
   administering to the patient an agent comprising a cartilage matrix production agent containing an anti-F as IgM antibody as an active ingredient and a pharmaceutically acceptable carrier by means of injection,
   wherein the patient having a disease classified as any of grade 1 to 3 according to the ICRS classification of osteoarthritis,
   wherein the anti-Fas IgM antibody is an agonist antibody against the extracellular domain of a Fas antigen, and wherein the anti-Fas IgM antibody is the only active ingredient.

6. The method as claimed in claim 5,
   wherein the anti-Fas IgM antibody is CH11 or 7C11.

* * * * *

SEQUENCE LISTING

<160> NUMBER OF SEQ ID NOS: 1

<210> SEQ ID NO 1
<211> LENGTH: 335
<212> TYPE: PRT
<213> ORGANISM: Homo sapiens

<400> SEQUENCE: 1

```
Met Leu Gly Ile Trp Thr Leu Pro Leu Val Leu Thr Ser Val Ala
1               5                   10                  15

Arg Leu Ser Ser Lys Ser Val Asn Ala Gln Val Thr Asp Ile Asn Ser
            20                  25                  30

Lys Gly Leu Glu Leu Arg Lys Thr Val Thr Val Glu Thr Gln Asn
            35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65              70                  75                  80

Asp Cys Val Pro Cys Gln Glu Gly Lys Glu Tyr Thr Asp Lys Ala His
                85                  90                  95

Phe Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Gly Phe Val Arg Lys Asn Gly Val Asn Glu
                245                 250                 255

Ala Lys Ile Asp Glu Ile Lys Asn Asp Asn Val Gln Asp Thr Ala Glu
            260                 265                 270

Gln Lys Val Gln Leu Leu Arg Asn Trp His Gln Leu His Gly Lys Lys
        275                 280                 285

Glu Ala Tyr Asp Thr Leu Ile Lys Asp Leu Lys Lys Ala Asn Leu Cys
    290                 295                 300

Thr Leu Ala Glu Lys Ile Gln Thr Ile Ile Leu Lys Asp Ile Thr Ser
305                 310                 315                 320

Asp Ser Glu Asn Ser Asn Phe Arg Asn Glu Ile Gln Ser Leu Val
                325                 330                 335
```